(12) United States Patent
Nishiura

(10) Patent No.: US 9,342,922 B2
(45) Date of Patent: May 17, 2016

(54) MEDICAL IMAGING APPARATUS AND METHOD OF CONSTRUCTING MEDICAL IMAGES

(75) Inventor: Tomofumi Nishiura, Tokyo (JP)

(73) Assignee: HITACHI MEDICAL CORPORATION, Tokyo (JP)

( * ) Notice: Subject to any disclaimer, the term of this patent is extended or adjusted under 35 U.S.C. 154(b) by 199 days.

(21) Appl. No.: 14/235,114

(22) PCT Filed: Jul. 25, 2012

(86) PCT No.: PCT/JP2012/068750
§ 371 (c)(1),
(2), (4) Date: Jan. 27, 2014

(87) PCT Pub. No.: WO2013/027526
PCT Pub. Date: Feb. 28, 2013

(65) Prior Publication Data
US 2014/0152661 A1 Jun. 5, 2014

(30) Foreign Application Priority Data
Aug. 19, 2011 (JP) .................................. 2011-179889

(51) Int. Cl.
*G06T 17/00* (2006.01)
*G06T 15/08* (2011.01)
(Continued)

(52) U.S. Cl.
CPC .............. *G06T 15/08* (2013.01); *A61B 8/0866* (2013.01); *A61B 8/145* (2013.01); *A61B 8/483* (2013.01);
(Continued)

(58) Field of Classification Search
CPC ..... G06T 15/08; G06T 15/506; G06T 15/005; G06T 17/20; G06T 7/0012; G09G 2340/0407; A61B 8/12; A61B 5/0408; A61B 18/1492; A61B 5/4362; A61B 8/4461; A61B 8/0883; A61B 5/0002; G01S 7/52074; G06F 19/322
USPC ......... 345/418, 419, 420, 423, 424, 426, 427, 345/428, 441, 530, 619, 660, 661, 664; 600/101, 103, 109, 300, 372, 373, 376, 600/437, 439, 440, 441, 442, 443, 444, 445, 600/467, 450; 128/920, 922, 923, 924
See application file for complete search history.

(56) References Cited

U.S. PATENT DOCUMENTS

2007/0258631 A1* 11/2007 Friedman .................. A61B 8/08
382/128
2007/0276214 A1* 11/2007 Dachille ............... G06T 7/0012
600/407
2009/0209859 A1 8/2009 Tsujita et al.

FOREIGN PATENT DOCUMENTS

| JP | A-2005-288153 | 10/2005 |
| JP | A-2006-130071 | 5/2006 |
| JP | A-2006-223712 | 8/2006 |

(Continued)

OTHER PUBLICATIONS

Nguyen, T. D., Kim, S. H., & Kim, N. C. (Jan. 2005): "An automatic body ROI determination for 3D visualization of a fetal ultrasound volume", In Knowledge-Based Intelligent Information and Engineering Systems (pp. 145-153), Springer Berlin Heidelberg.*

(Continued)

*Primary Examiner* — Xiao Wu
*Assistant Examiner* — Sarah Lhymn
(74) *Attorney, Agent, or Firm* — Oliff PLC

(57) ABSTRACT

Apparatus and method of medical diagnostic imaging. The apparatus includes: an image unit for constructing volume image data by capturing images from a multiplicity of tomographic images of a sampling specimen and for constructing internal three dimensional images of the diagnosing object of the sampling specimen as seen from a viewing point; a display for displaying the three-dimensional images; an input unit for entering parameters for setting up a precutting plane at an inter-voxel image data boundary between voxel image data of the volume image data closer to the viewing point than the diagnosing object and voxel image data associated with the diagnosing object; and a control unit for controlling the structure of the three-dimensional images constructed by the image unit based on the precutting plane set up via the input unit, wherein the control unit extracts a boundary based on one of the parameters inputted to the input unit.

6 Claims, 18 Drawing Sheets

(51) Int. Cl.
*A61B 19/00* (2006.01)
*A61B 8/08* (2006.01)
*A61B 8/14* (2006.01)
*G06T 19/00* (2011.01)

(52) U.S. Cl.
CPC .................. *A61B 19/50* (2013.01); *G06T 19/00* (2013.01); *G06T 2210/41* (2013.01); *G06T 2219/008* (2013.01)

(56) References Cited

FOREIGN PATENT DOCUMENTS

JP  2010-148828 A  7/2010
WO  WO 2006/085571 A1  8/2006

OTHER PUBLICATIONS

International Search Report issued in International Patent Application No. PCT/JP2012/068750 dated Oct. 9, 2012 (with translation).

* cited by examiner

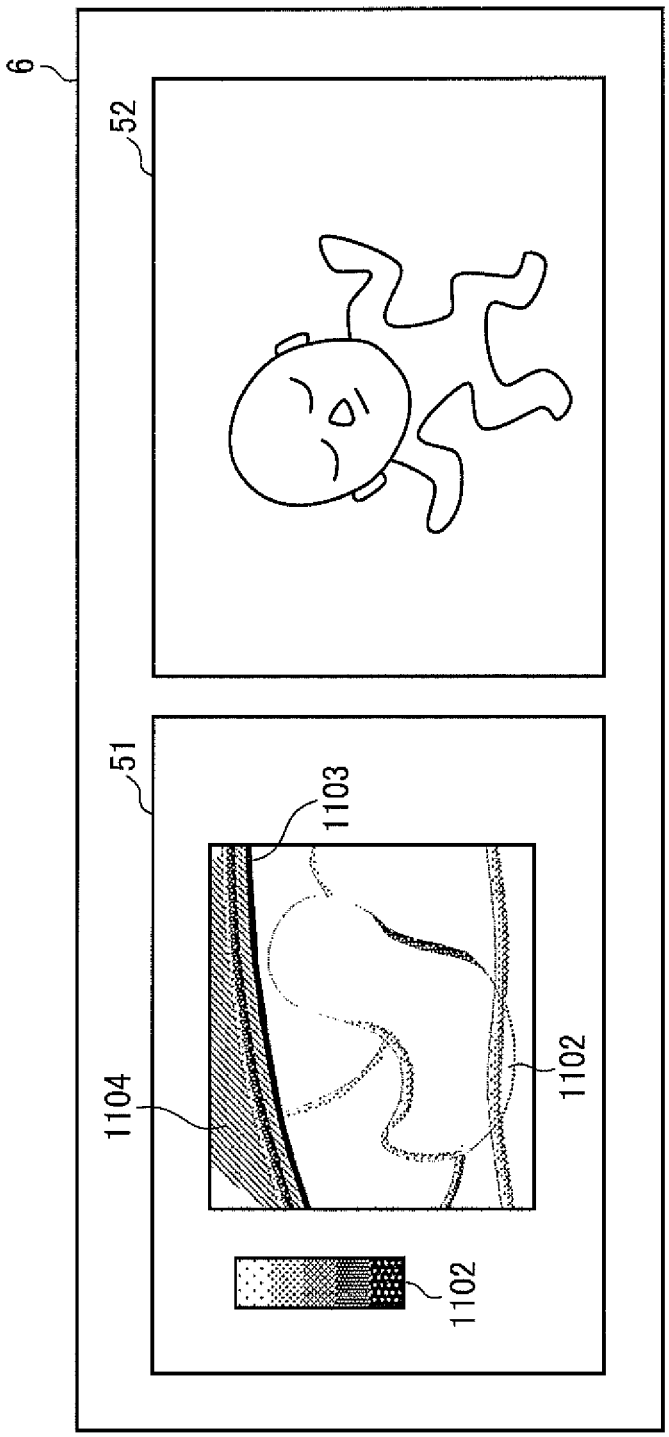

MEDICAL IMAGING APPARATUS AND METHOD OF CONSTRUCTING MEDICAL IMAGES

TECHNICAL FIELD

This invention relates to a medical imaging apparatus and a method of constructing medical images, and more particularly to a medical imaging apparatus and a method adequate to construct and display a three-dimensional image of a diagnosing object.

BACKGROUND ART

The medical imaging apparatus including such as an ultrasonic imaging apparatus or a magnetic resonance imaging apparatus obtains the image of a portion of the diagnosing object that includes a fetus and constructs a three-dimensional image of the fetus using a volume rendering method for example, and display the three-dimensional image on a display screen.

The volume rendering method constructs, using the volume image data of the diagnosing object, a three-dimensional image of the fetus as seen from an arbitrary viewing point based on a plural of voxel image data that lie on the line of sight to the fetus.

However, since voxel data of a placenta are located closer to the viewing point than the voxel data of the fetus, a clear image of the fetus cannot be obtained from the volume data that contain voxel data of the placenta and the fetus due to the fact that the voxel image data the placenta affect the image of the fetus.

Thus, in order to obtain a clear three-dimensional image of the fetus, voxel image data lying between the viewing point and a precutting plane established at a precutting line set up at a point on the line of sight are removed so that a clear three-dimensional image of the fetus can be constructed from the remaining voxel image data. (See, for example, Patent Document 1 listed below.)

PRIOR ART REFERENCES

Patent Documents

Patent Document 1: JPA 2005-288153

BRIEF SUMMARY OF THE INVENTION

Object to be Solved by the Invention

It is noted in the Patent Document 1, however, that since a diagnostician sets up a precutting plane based on a single precutting line, the depth-wise validity of the precutting plane established cannot be confirmed by the diagnostician until the diagnostician actually looks at a displayed three dimensional image of the fetus constructed.

It is therefore an object of the present invention to provide a medical imaging apparatus capable of confirming the validity of a precutting place to be set up. It is another object of the invention to provide a method of constructing a medical image that permits confirmation of the validity of such precutting plane.

Means for Achieving the Object

The present invention is adapted to: acquire volume image data composing plural number of cross-section region images of a diagnosing object obtained on the plural number of cross sections perpendicular to a line passing through the cross-section region images; construct a three-dimensional image of a diagnosing target of the diagnosing object as seen from a set viewing point, using the volume image data; display the cross-section region images of the diagnosing object or the three dimensional image of the diagnosing target; input parameters that includes parameters for setting up a precutting plane at an inter-voxel image data boundary between those voxel image data closer to the viewing point than the voxel image data associated with the diagnosing target of the diagnosing object and those voxel image data associated with the diagnosing target of the diagnosing object, using the cross-section region images of the diagnosing object displayed; control configuration of the three dimensional image of the diagnosing target based on the precutting plane thus set up; extract the inter-voxel image data boundary between the voxel image data based on a threshold value included in the setup parameters; reset the precutting plane based on the extracted boundary; and control configuration of the three dimensional image of the diagnosing target based on the precutting plane obtained by reset precutting plane.

Results of the Invention

The present invention can provide an apparatus and a method of constructing medical images. The invention permits confirmation as to whether or not a precutting plane is properly set up.

BRIEF DESCRIPTION OF THE DRAWINGS

FIG. 18 illustrates a further precutting plane setting screen along with a three-dimensional image constructed.

BEST MODE FOR CARRYING OUT THE INVENTION

A medical imaging diagnostic apparatus according to a first embodiment of the invention will now be described in detail by way of example with reference to the accompanying drawings. The medical diagnostic apparatus can be any of an MRI apparatus, an X-ray CT apparatus, and an ultrasonic apparatus, so long as it can provide cross-section region images of a diagnosing portion (target) of a diagnosing object.

An MRI apparatus generates cross-section region images from two- or three-dimensional position data, obtained by observing under an inclined magnetic field relaxation signals emitted from different tissues of a diagnosing object subjected to an external static magnetic field.

An X-ray CT apparatus irradiates a diagnosing object with X-rays from all directions emitted by an X-ray source that rotates round the examining object together with an X-ray detector. The irradiated X-ray is partly absorbed by the examining object, but a dissipated X-ray is detected and recorded by an X-ray detector located across the examining object. After all directive absorption data are registered, the data are Fourier analyzed by a computer to construct cross-section region images.

The present embodiment is concerned with a typical medical imaging apparatus adapted to construct three-dimensional images of a diagnosing portion from cross-section region images of the diagnosing object obtained by an ultrasonic diagnostic apparatus. It is noted, however, that the above mentioned MRI apparatus and X-ray CT apparatus can be alternatively used to acquire the cross-section region images.

Figure 1:
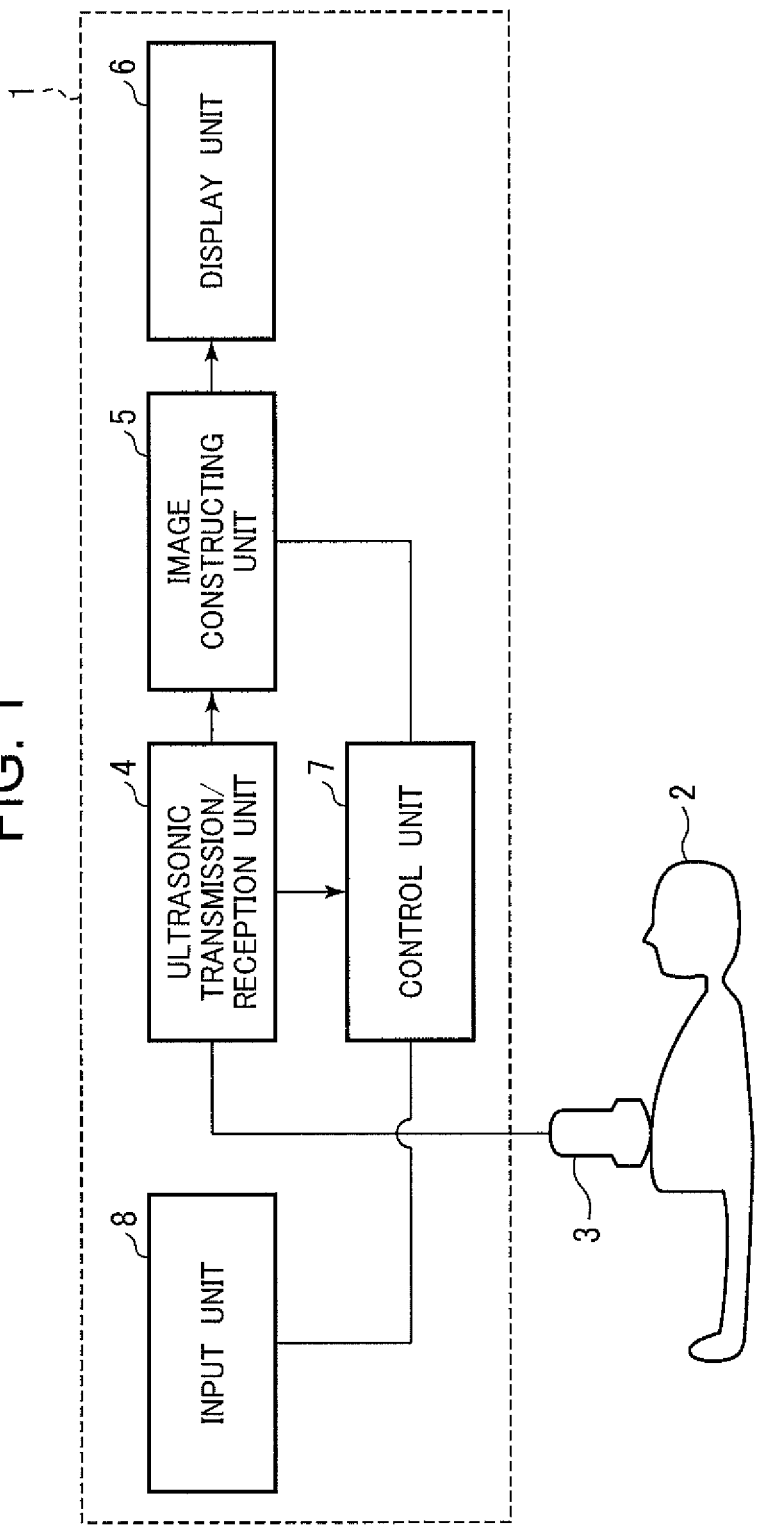
FIG. 1 is a block diagram showing a medical imaging apparatus according to one embodiment of the invention.

As shown in FIG. 1, an ultrasonic diagnostic apparatus 1 of the present embodiment transmits an ultrasonic wave to a diagnosing object 2 and detects reflected echo signals from the diagnosing object 2 to construct two- or three-dimensional ultrasonic images of a diagnosing object. The images may be displayed on a screen.

The ultrasonic diagnostic apparatus 1 has an ultrasonic probe 3 equipped with a multiplicity of transducers for emitting/receiving the ultrasonic wave to/from an diagnosing object 2; an ultrasonic transmission/reception unit 4 for providing the ultrasonic probe 3 with ultrasonic signals; an image constructing unit 5 for constructing two-dimensional cross-section region images from signals received, and for constructing three-dimensional images from the cross-section region images; a display unit 6 for displaying the cross-section region images and three-dimensional images constructed by the image constructing unit 5; a control unit 7 for controlling the above-mentioned units; and an input unit 8 for providing the control unit 7 with diagnostician's instructions.

The ultrasonic probe 3 has a multiplicity of transducers arrayed in the direction of its long-axis. Each of the transducers is cut up into a multiplicity of transducer elements in the short-axis direction perpendicular to the long-axis direction.

The ultrasonic transmission/reception unit 4 has a function for focusing the transmitting and receiving waves by controlling transmitted and received timing of the ultrasonic wave between the transducers and the transducer elements which are arrayed in the long axis direction of the probe 3 as well as in the short axis direction perpendicular thereto.

Also, the ultrasonic transmission/reception unit 4 is adapted to obtain three-dimensional volume image data that include plural number of cross-section region images by scanning the scanning planes not only in the long-axis direction but also in the short-axis direction when scanning for transmitting wave and receiving waves. The ultrasonic probe 3 and the ultrasonic transmission/reception unit 4 can be of any structure so long as they can obtain multiple cross-section region images and convert them into three dimensional volume image data.

The display unit 6 comprises a display screen, for example a CRT monitor and an LCD monitor. The display unit 6 displays cross-section region images converted by the image constructing unit 5.

The control unit 7 is a control computer system, consisting of the display unit 6 and the input unit 8, for controlling the ultrasonic transmission/reception unit 4 and image constructing unit 5 based on the information (inputted parameters) including instructions inputted to the input unit 8. Upon receipt of reflected echo signals from the ultrasonic transmission/reception unit 4, the control unit 7 transfers the echo signals to the image constructing unit 5, where the signals are converted into cross-section region images and three dimensional images, which are sent to the display unit 6 along with the image information to be displayed together on.

Figure 2:
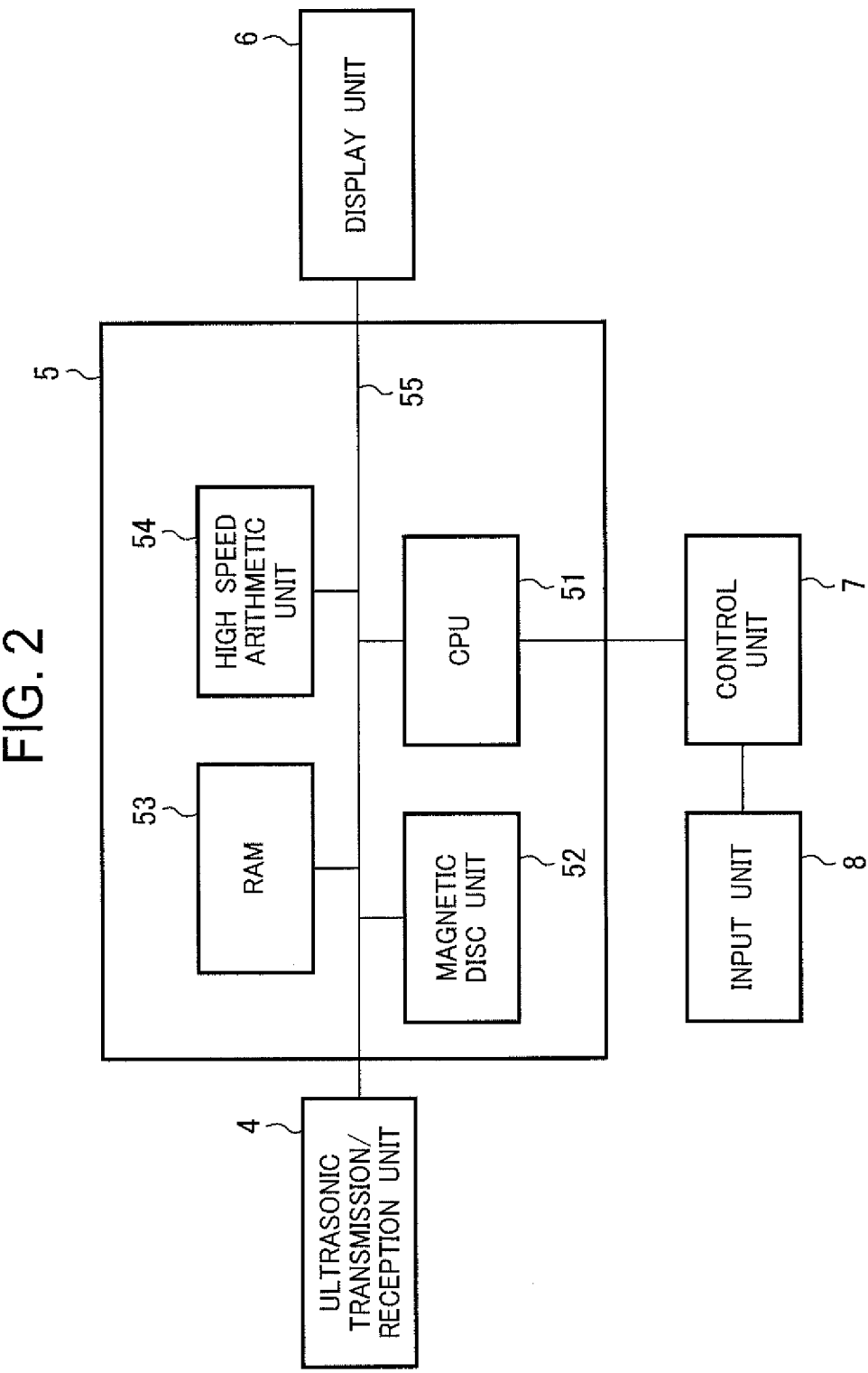
FIG. 2 is a block diagram showing the hardware arrangement of an image constructing unit 5 shown in FIG. 1 and its peripheral unit.

Referring to FIG. 2, structural features of the image constructing unit 5, control unit 7, and input unit 8 of the present invention will now be described.

The image constructing unit 5 has a central processing unit (CPU) 51, a magnetic disc 52, a RAM 53, and a high-speed arithmetic unit 54, all connected together with a bus 55.

The CPU 51 is connected to the control unit 7, from which a control program can be transmitted to the CPU 51. The bus 55 connects the output end of the ultrasonic transmission/reception unit 4 to the input end of the display unit 6

The CPU 51 controls the magnetic disc 52, RAM 53, and the high-speed arithmetic unit 54 in accord with the control program provided from the control unit 7. The magnetic disc 52 stores the reflected echo signals and RF signals outputted from the ultrasonic transmission/reception unit 4. The RAM 53 is used as a work memory to retrieve the reflected echo signals and the RF signals from the magnetic disc 52 and to construct cross-section region images from the reflected echo signals, or construct three dimensional images from the cross-section region images. The high-speed arithmetic unit 54 performs computations for constructing cross-section region images from the reflected echo signals and constructing three dimensional images from the cross-section region images.

Figure 3:
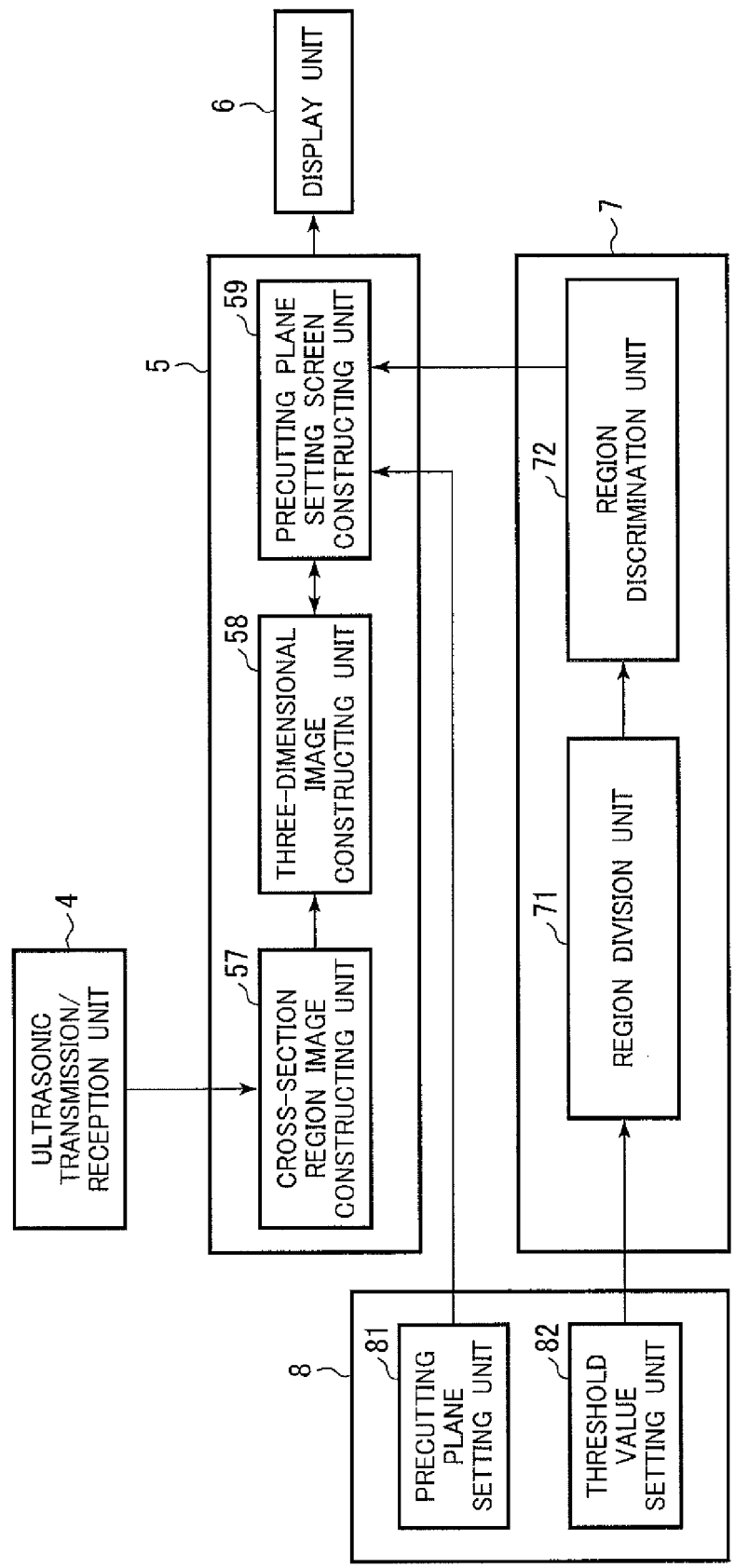
FIG. 3 is a block diagram showing the functions of the image constructing unit 5 and its peripheral units.

Next, referring to FIG. 3, functions of the image constructing unit 5, control unit 7, and input unit 8 will be described. The input unit 8 has a precutting plane setting unit 81 for setting the precutting plane to the cross-section region images or three dimensional images displayed on the display unit 6, and a threshold value setting unit 82 for setting a threshold value of boundary voxels that bounds a three dimensional region associated with the diagnosing target of the diagnosing object and the three dimensional regions adjacent to the diagnosing target.

The image constructing unit 5 has: a cross-section region image constructing unit 57 for converting into cross-section region images reflected echo signals received from the ultrasonic transmission/reception unit 4; a three-dimensional image constructing unit 58 for constructing volume image data by capturing images from plural number of cross-section region images of a diagnosing object in the direction perpendicular to the planes of the cross-section region images to thereby obtain volume image data, and for constructing internal three-dimensional images of a diagnosing target of the diagnosing object as seen from a viewing point set up on the basis of the volume image data; and a precutting plane setting-screen constructing unit 59 for constructing a precutting plane to be displayed on the display unit 6 upon receipt of data inputted to a precutting plane setting unit 81 and a region discrimination unit 72.

The precutting plane setting-screen constructing unit 59 superimposes a divided line of the cross-section region image and a divided line of the entire three-dimensional image as a boundary line with a precutting line belonging to the precutting plane set up by the precutting plane setting unit 81. When the boundary is a plane instead of a line, the boundary plane is superimposed with the precutting plane.

The control unit 7 is equipped with a region division unit 71 that divides volume image data into plural number of three dimensional regions (Step S12, FIG. 4) by evaluating each of the plural number of voxel image data, along with the region discrimination unit 72, which is adapted to discriminate at least one of the three dimensional region associated with the diagnosing target, for example amniotic fluid, from the three dimensional region adjacent thereto, and to reset a boundary between the discriminated three dimensional region associated with the diagnosing target and adjacent regions or to reset a precutting plane in a three dimensional region adjacent the diagnosing target (by executing Step S14 shown in FIG. 4), on the basis of the voxel image data belonging to the respective three dimensional regions.

In the example shown herein, the region division unit 71 and the region discrimination unit 72 are provided in the control unit 7. Alternatively, however, they may be provided in the CPU 51.

It is noted that the precutting plane setting-screen constructing unit 59 of the image constructing unit 5 generates precut volume image data, with the voxel data lying between the reset precutting plane and the viewing point deleted. That is, the precutting plane setting-screen constructing unit 59 has a function to execute a procedure of Step S15 shown in FIG. 4.

Figure 4:
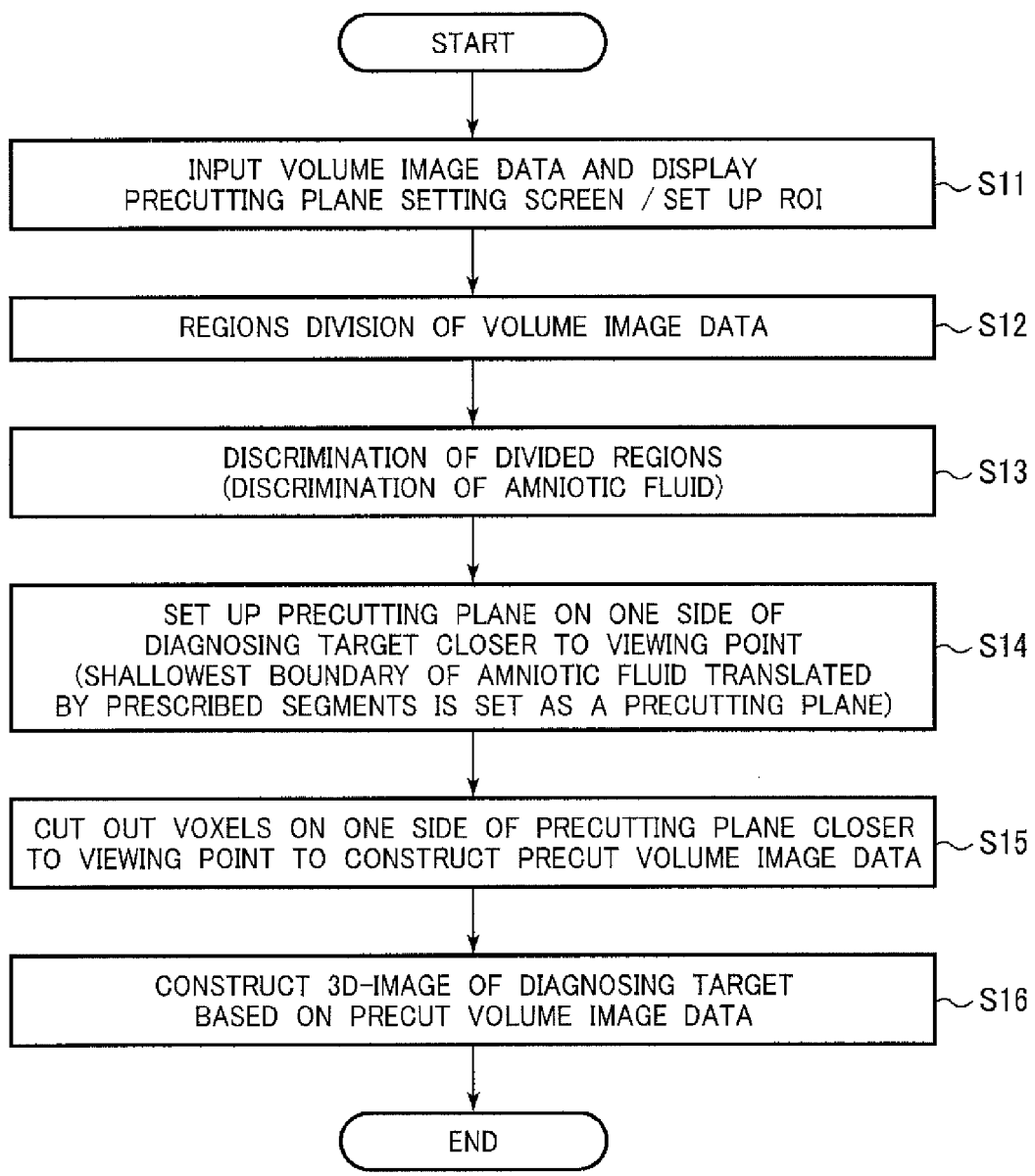
FIG. 4 is a flowchart illustrating the characteristic arrangement of the apparatus according to said embodiment.

The three-dimensional image constructing unit 58 of the image constructing unit 5 constructs a three dimensional image of the diagnosing target based on the precut volume image data, in accord with Step S16 shown in FIG. 4.

The control unit 7 transmits the cross-section region images and three dimensional images constructed by the image constructing unit 5 to the display unit 6.

The display unit 6 displays image information including the cross-section region images and the three-dimensional images.

The image constructing unit 5 may have different characteristic modes, as exemplified in the embodiments disclosed below.

Embodiment 1

FIG. 4 is a flowchart in accordance with a first embodiment of the invention showing a procedure carried out by a program provided by the image constructing unit 5.

Figure 5:
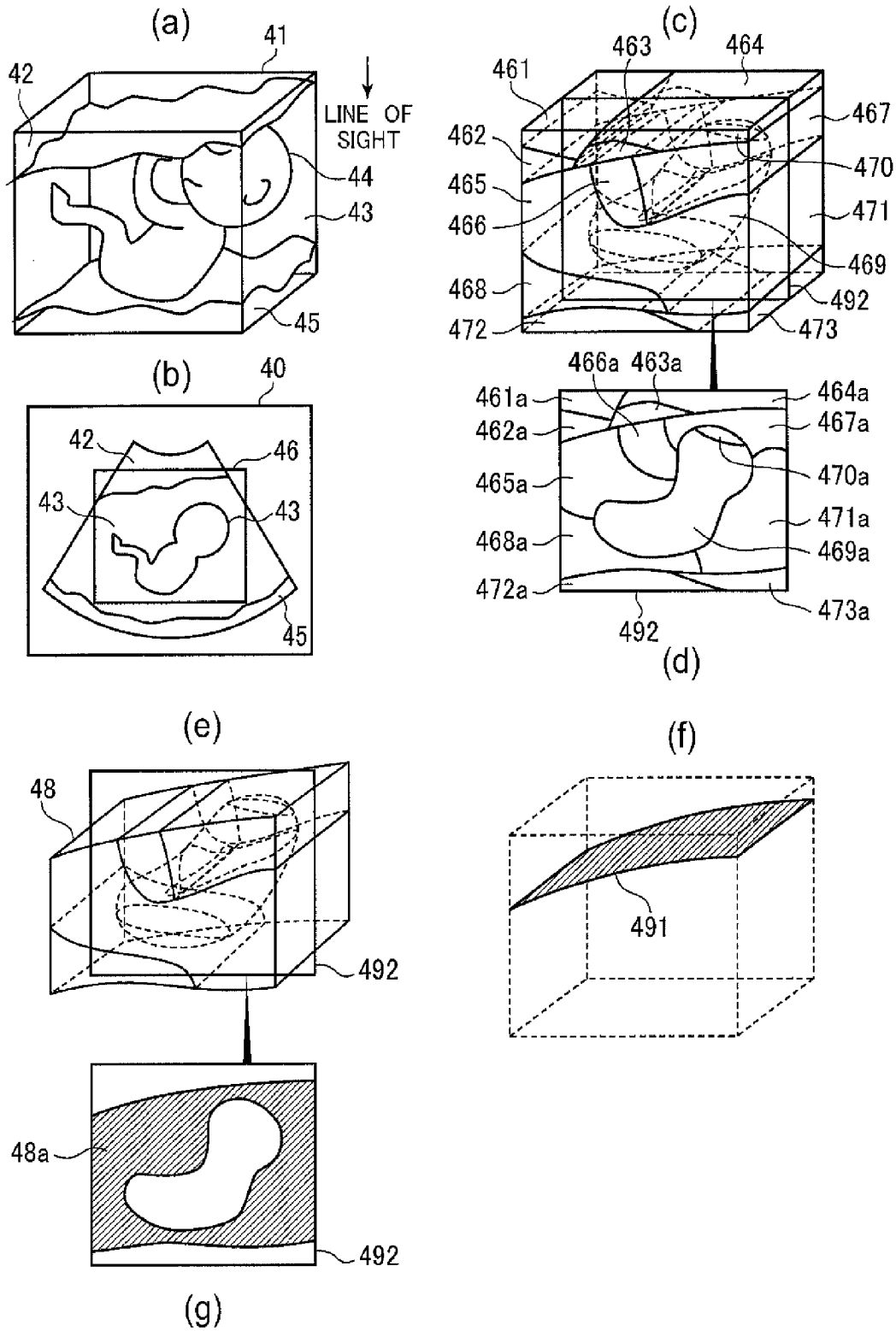
FIG. 5 is exemplary ultrasonic images used to explain the flowchart of FIG. 4.

First, in Step S11 for inputting volume image data and for setting up a precutting plane setting screen or ROI, the image constructing unit 5 enters volume image data and displays a precutting plane setting screen on the display unit 6. With the precutting plane setting screen displayed on the display unit 6, a diagnostician enters data for setting an ROI in the input unit 8. Referring now to FIG. 5, a specific example is described, in which a diagnosing target is a fetus. In this case, the diagnostician sets a three-dimensional ROI 46 on the two-dimensional precutting plane setting screen 40 on the display unit 6, as shown in FIG. 5(b). The volume image data 41 set by the ROI 46 will be imaged as shown in FIG. 5(a) when converted into a three-dimensional image. A fetus 44 inside the uterine mucous membrane 45 is fed by the placenta 42 as shown in FIG. 5(a).

In the next region dividing step, S12 shown in FIG. 4, the region division unit 71 divides the three-dimensional volume image data 41 into plural number of three-dimensional region (hereinafter referred to as segments) based on the respective voxel image data. In other words, the region division unit 71 executes region dividing procedure on the volume image data 41 specified by the ROI 46. In this region dividing procedure, the volume image data 41 is divided into segments 461-473. The group of voxels of the placenta 42 are correspond to the segments 461-464, the voxels of the amniotic fluid 43 to the segments 465-467 and 471, the voxels of fetus 44 to the segments 468 and 470, and the voxels of the uterine mucous membrane 45 to the segments 472 and 473. In this manner, the volume image data are divided, in the region dividing procedure of Step S12, into one or more segments indicative of the placenta 42, amniotic fluid 43, fetus 44 and uterine mucous membrane 45. The region dividing procedure of Step S12 is performed on a three-dimensional image data. As a result, if resultant regions of the region division are cut along the cross section 492 shown in FIG. 5(c), the segment 461 of the region 461a and the segment 462 of the region 462a appear, as shown in FIG. 5(d).

Thus, the region dividing procedure determines plural number of non-overlapping setting values and allowable ranges thereof in accordance with the voxel image data of the respective biological structures and portions of biological tissues, and divides voxel image data into plural number of three-dimensional regions by grouping voxels in accordance with their voxel values that fall in the same prescribed range.

Incidentally, there has been a well-known region dividing procedure, called method of clustering in a feature space. Other region dividing procedures include a mean shift method (Reference 1) and a graph cut method (Reference 2).

(Reference 1) Kazunori Okada, Research Report on Computer Vision and Image Media Vol. 2008, No. 27, PP. 401-414;

(Reference 2) Hiroshi Ishikawa, Information Processing Society Search Report Vol. 2007, No. 31, pp. 193-204.

In detecting a boundary of a three-dimensional region by region dividing procedure, such voxel image data of the density, density gradient, and other physical quantities related to these values in combination. In the embodiment 1, the region dividing procedure has been described in conjunction with acquisition of those regions associated with placenta 42, amniotic fluid 43, fetus 44, and uterine mucous membrane 45. However, it should be understood that the above procedure are not limited to these examples. For example, the procedure may be also applied to other types of extracting region that has a portion to be removed by an inventive precutting plane and volume image data 41 that needs resetting of a precutting plane.

The resultant divided regions are stored as segment information in either a magnetic disk unit magnetic disc 52 or RAM 53. Each piece of the segment information carries at least one of such information as a representative three-dimensional coordinate (for example, center of gravity of the segment), density of the voxel image data pertinent to the segment, and an identification code to uniquely identify the segment.

In order to reduce execution time required to divide the entire three-dimensional image data 41 as described above, a more convenient scheme may be employed in place of performing region division of the entire three-dimensional volume image data 41. For example, one array direction of the volume image data 41 is chosen to set up plural number of two-dimensional cross sections taken in sequence along that direction. Then, two-dimensional region division is performed on each of the two-dimensional cross sections to obtain two-dimensional segments. A three-dimensional segment is obtained by connecting the two-dimensional segments neighboring of a plural number of two-dimensional cross sections.

It is noted that when the diagnosing target is a fetus 44, it is likely that the amniotic fluid 43 lies closer to the viewing point than the fetus 44. If this is the case, region division may be performed only once for convenience between the fetus 44 and the amniotic fluid 43 to reduce region dividing time.

Next, in Step S13 of FIG. 4, the region discrimination unit 72 discriminates the three-dimensional region consisting of plural number of voxels associated with the diagnosing target of fetus 44 from voxels associated with other biological regions such as a placenta 42, an amniotic fluid 43, and any other biological three-dimensional region. As described in conjunction with the region dividing Step S12, such discrimination between the placentas 42, amniotic fluid 43, and fetus 44 can be made by determining whether the voxel image data 44 have values within a preset range assigned to a particular biological region. For example, of the divided segments 461-473, a group of segments associated with voxel data having a density value less than a predetermined value is determined as amniotic fluid segments 48, as shown in FIG. 5(*e*).

The procedure of discriminating a region may be performed by discriminating at least one of the three-dimensional regions associated with the diagnosing target and three-dimensional regions adjacent the diagnosing target on the basis of voxel value of respective three-dimensional regions, differences or gradients of the voxel value of neighboring voxels or one or more of these physical quantities in combination.

In order to remove from the volume image data 41 those segments, e.g. segments of the placenta 42, that lie closer to the viewing point than the fetus 44, those segments, of the segments 461-473, whose representative voxel image data has a lower density value than a predetermined level are recognized in a precutting plane setting procedure, Step S14 to be amniotic fluid segments 48. In the example shown in FIG. 5(*c*), segments 465,466,467, 468, and 471 satisfy the above condition, so that they constitute the amniotic fluid segments 48 shown in FIG. 5(*e*). If the segments 48 are cut along the cross section 492, a region 48*a* of FIG. 5(*g*) appears. In the next Step S14, volume image data 41 of the amniotic fluid segments 48 are divided into two portions separated by a plane 491 that has a shallowest depth, and the segment information associated with the portion of the segment having a shallower depth is added with a cutting segment mark. The cutting segment is a segment that is to be deleted without being used as a precut volume image data 41 that should form a basis of the three dimensional image of the diagnosing target. On the other hand, the segment information associated with a remnant segment having a deeper depth is added a remnant segment mark. The remnant segment is a segment which is left undeleted as a precut volume image data 41 to construct a three-dimensional image of the diagnosing target.

Figure 6:
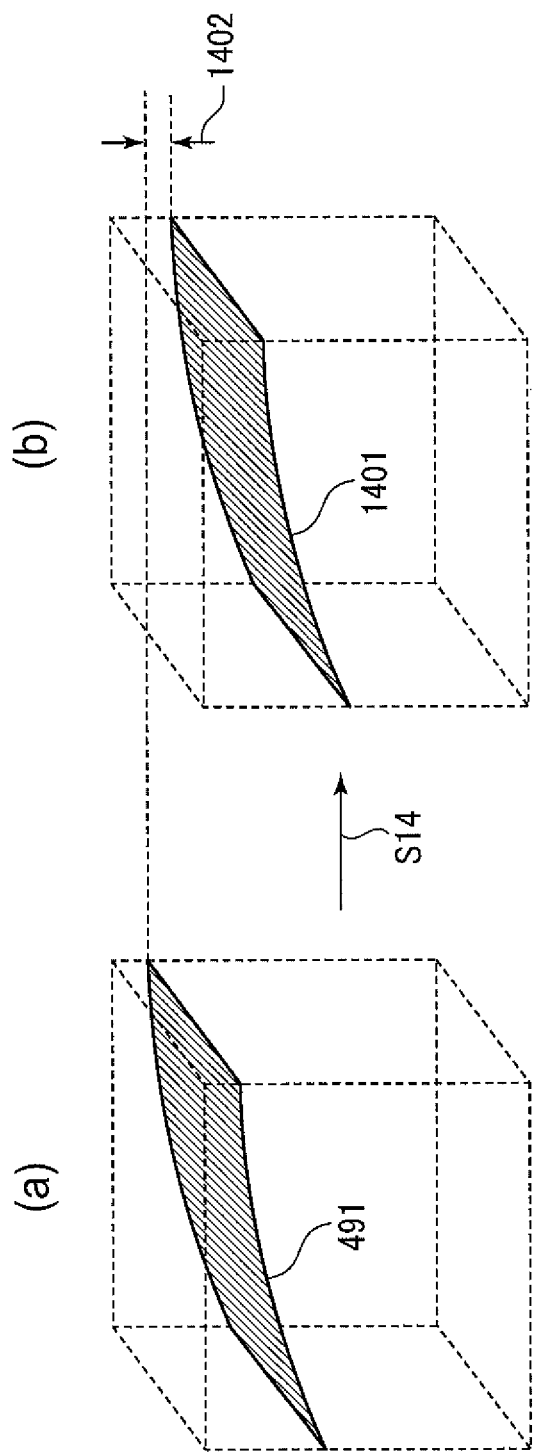
FIG. 6 illustrates a procedure of resetting a precutting plane according to the flowchart of FIG. 4.

Next, as shown in FIG. 6, the shallowest plane 491 consisting of voxels having a shallow depth in the amniotic fluid segments 48 is moved towards a still deeper direction by a predetermined number (N voxels) of voxels 1402 to set it up as a precutting plane 1401. Where the predetermined number (N voxels, with N being a number greater than zero) of voxels 1402 is a parameter required to unmistakably treat the portion in contact with the amniotic fluid segment 48 as a segment to be cut. In order to reduce noises in the three-dimensional image of the fetus 44, the precutting plane 1401 may be smoothed and reset as a smooth precutting plane.

As described above in conjunction with the first embodiment, the region division unit 71 divides the volume image data into a plural number of three-dimensional regions in accord with the respective voxel image data; the region discrimination unit 72 discriminates at least one of the three-dimensional region associated with the diagnosing target and the three-dimensional region adjacent the diagnosing target based in accord with the volume image data divided by the region discrimination unit 72; and the control unit 7 sets up a precutting plane at a boundary between a three-dimensional region associated with a diagnosing target discriminated by the region discrimination unit 72 and a three-dimensional region adjacent thereto, or in the three-dimensional region adjacent the diagnosing object.

That is, in the embodiment 1, each of the voxels constituting the volume image data is discriminated according to whether its voxel value has the value of the diagnosing object (e.g. fetus) or not. Such discrimination of different diagnosing objects is made possible by collecting particular voxel values of different diagnosing targets. If it is possible to discriminate a particular three-dimensional region of voxels association with a diagnosing object, it is easier to set up a precutting plane on one side of the three-dimensional region of the diagnosing target closer to the viewing point. As a result, the diagnostician can confirm whether or not the precutting plane is properly set in the perspective direction. Thus, an optimum precutting plane can be set up to obtain a clear three-dimensional image of the diagnosing target of the diagnosing object without deleting any of the volume image data of the diagnosing target.

In the embodiment 1, it is also possible to set up a curved precutting surface on one side of the three-dimensional region of the diagnosing object closer to the viewing point (the side referred to as viewer side), thereby enabling totally precutting regions other than those associated with the diagnosing target. Consequently, a still clear three-dimensional image of the diagnosing target can be obtained. It is also possible to determine those voxels having voxel values within a prescribed range to be the voxels associated with the diagnosing target. It is preferable to provide variable setting values and ranges for discriminating voxels so that the setting values and ranges can be adjusted to obtain an appropriate three-dimensional image of a preferred diagnosing target at the time of diagnosis.

It is also noted that in the method of setting up a precutting plane of the embodiment 1 is capable of discriminating those voxels having voxel values within a prescribed range to be neighboring voxels surrounding the diagnosing target of the diagnosing object, and setting up a precutting plane within a three-dimensional region associated with the neighboring voxels closer to the viewing point. In the case where the diagnosing target is a fetus, for example, it is normally surrounded by amniotic fluid whose voxels have significantly lower voxel values than that of the fetus, so that the three-dimensional image of the fetus is not changed appreciably if the voxels of the amniotic fluid is entirely deleted. Furthermore, since the dimension of the amniotic fluid region is relatively large, discrimination of the amniotic fluid is easy.

It is therefore possible to correctly construct a clear three-dimensional image of the diagnosing target of the diagnosing object by discriminating the three-dimensional region of the amniotic fluid and setting up a precutting plane within the amniotic fluid region, without entirely deleting the volume image data of the diagnosing object.

The precutting plane setting unit of the medical imaging apparatus of the embodiment 1 may be comprised of a region division unit for dividing the volume image data into plural number of three-dimensional regions based on the voxel values of said plural number of voxels, and a region discrimination unit for discriminating at least one of the three-dimensional region associated with the diagnosing target and the three-dimensional regions adjacent the diagnosing target, based on the voxel values of the respective volume image data divided by the region division unit. In this case, the precutting plane setting unit may be configured to set up a precutting plane at a boundary either between the three dimensional region associated with the diagnosing target discriminated by the region discrimination unit or in the three dimensional region adjacent the diagnosing target.

The embodiment 1 is basically characterized by its capability of dividing the volume image data into plural number of three-dimensional regions based on the voxel values of the volume image data. Normally, a diagnosing target is surrounded by various biological structures and tissues. Therefore, a specific voxel value pertinent to a particular diagnosing region as well as plural number of non-overlapping setting values and tolerance ranges in difference from the setting values is set in accordance with the voxel values of the diagnosing region. That is, by grouping those voxels that have voxel values within a tolerance range pertinent to the group, volume image data can be divided into plural number of three-dimensional regions associated with the respective biological regions. It is noted that if one or more of the three dimensional regions adjacent a particular diagnosing region is (are) discriminated, a preferred precutting plane can be set up in (one of) the adjacent three-dimensional region without deleting any of the volume image data, and an internal clear three-dimensional image of the diagnosing target of the diagnosing object can be established.

The region discrimination unit of the embodiment 1 can discriminate at least one of the three-dimensional regions associated with the diagnosing target and the three-dimensional regions adjacent the diagnosing target, based on such physical quantities as the voxel value, difference or gradient of voxel value between two neighboring voxels, or a combination thereof.

Furthermore, the precutting plane setting unit of the embodiment 1 can set up the above-mentioned precutting plane between the shallowest boundary of the three-dimensional region associated with the diagnosing target as seen from the viewing point, and the deepest boundary of the three-dimensional region as seen from the viewing point as discriminated by the region discrimination unit. In the case where the diagnosing target is a fetus, a risk of partly deleting the image of the fetus and a risk of partly leaving the image of the placenta can be reduced, since amniotic fluid voxels affect the sharpness of the three-dimensional fetus image only slightly.

The image constructing unit of the embodiment 1 may further construct at least one of a cross sectional region image taken on an arbitrary cross section displayed of plural number of three-dimensional regions and an overall three-dimensional image of the multiple three-dimensional regions, based on the volume image data divided by the region division unit, and has a precutting plane setting screen construction unit adapted to construct a precutting plane setting screen superposed with a precutting line or plane set up via the input unit the cross sectional image, a boundary line or plane, shown in the overall three-dimensional image, of the divided three-dimensional regions, and display on the display unit the precutting plane setting screen. With this configuration, the diagnostician can easily grasp correct positional relationship between the diagnosing object shown in the cross-section region images and the three dimensional image and other biological regions relative to the precutting plane, and hence confirm if the precutting plane is properly set up. In this case, the cross-section region images are preferably shown in three orthogonal cross sections, which consist of orthogonal three cross sections of the volume image data.

Furthermore, the precutting plane setting screen preferably shows the three-dimensional region to be deleted along with the residual three-dimensional region in different display modes. Accordingly, upon confirmation of the precutting plane set up, the diagnostician can easily modify the position of the precutting plane in terms of three dimensional regions if he wishes so.

In short, the precutting plane setting screen constructing unit is preferably configured such that, when a three-dimensional region adjacent the precutting plane or line is selected via the input unit, the precutting plane adjacent the selected three-dimensional region is moved towards, or away from, the viewing point. In this case, the precut setting screen preferably reflects the following changes, the three-dimensional region on one side of the precutting plane proximal to the viewing point is marked with a remnant candidate and the three-dimensional region on the other side is marked with a cutting candidate which are well distinguishable in color or shape from each other. This helps the diagnostician perform modification operations more conveniently.

The apparatus of the embodiment 1 may be further equipped with a precut three-dimensional image construction unit that constructs a three-dimensional image of a residual three-dimensional region of the precut volume image data and displays the resultant image on the image display unit.

More particularly, the embodiment 1 has a fundamental feature that the volume image data is divided into plural number of three-dimensional regions based on the voxel image data. It is noted that a diagnosing target is normally surrounded by biological regions of different biological structures and tissues. The embodiment 1, therefore, determines plural number of setting values and plural number of tolerance ranges in difference of non-overlapping setting values from the setting values in accordance with the voxel image data of a particular diagnosing region and of different biological structures and the biological tissues. That is, the volume image data can be divided into plural number of three-dimensional regions pertinent to the respective biological regions by grouping voxel image data such that voxels of each group have voxel values within a tolerance range pertinent to the group. It is noted that if one or more three-dimensional regions adjacent a particular diagnosing region are discernible, a precutting plane can be set up within one of the adjacent three-dimensional region, so that a clear three-dimensional image of the diagnosing target of the diagnosing object can be unmistakably constructed without deleting the volume image data of the diagnosing object.

A region discrimination unit 72 of the embodiment 1 can discriminate at least one of the three-dimensional regions associated with the diagnosing target and three-dimensional regions adjacent the diagnosing target on the basis of voxel values of respective three-dimensional regions, differences or gradients of the voxel values of neighboring voxels, or a physical quantities in combination of these values.

Furthermore, the region discrimination unit 72 of the embodiment 1 discriminates between the shallowest boundary as seen from the viewing point of a three-dimensional region associated with the diagnosing target and the deepest boundary as seen from the viewing point of a neighboring three-dimensional region, and outputs the result of the discrimination to the precutting plane setting unit 81 to set up a precutting plane. In this way, when the diagnosing target is a fetus for example, it is possible to eliminate the risk of deteriorating in part the voxel image data of the fetus and the risk of leaving in part the voxel data of the placenta, since the voxels of amniotic fluid do not greatly affect the clarity of the three-dimensional image of the fetus. Thus, the voxel image data of the fetus may be well preserved.

Furthermore, based on the volume image data divided by the region discrimination unit 72, the image constructing unit 5 of the embodiment 1 can construct at least a cross sectional image taken at an arbitrary cross section of plural number of three-dimensional regions and indicating said plural number of three-dimensional regions and an overall three-dimensional image of said plural number of three-dimensional regions.

By providing the apparatus with a precutting plane setting screen constructing unit 56, the diagnostician can easily grasp positional relationships between the diagnosing target displayed in the construct of a cross-section region image or a three-dimensional image, images of other biological regions, and a precutting plane, so that he can confirm if the precutting plane is adequate or not. In this case the cross-section region image can be shown in a three-cross sectional image obtained by slicing volume image data in the three orthogonal cross sections.

Embodiment 2

Figure 7:
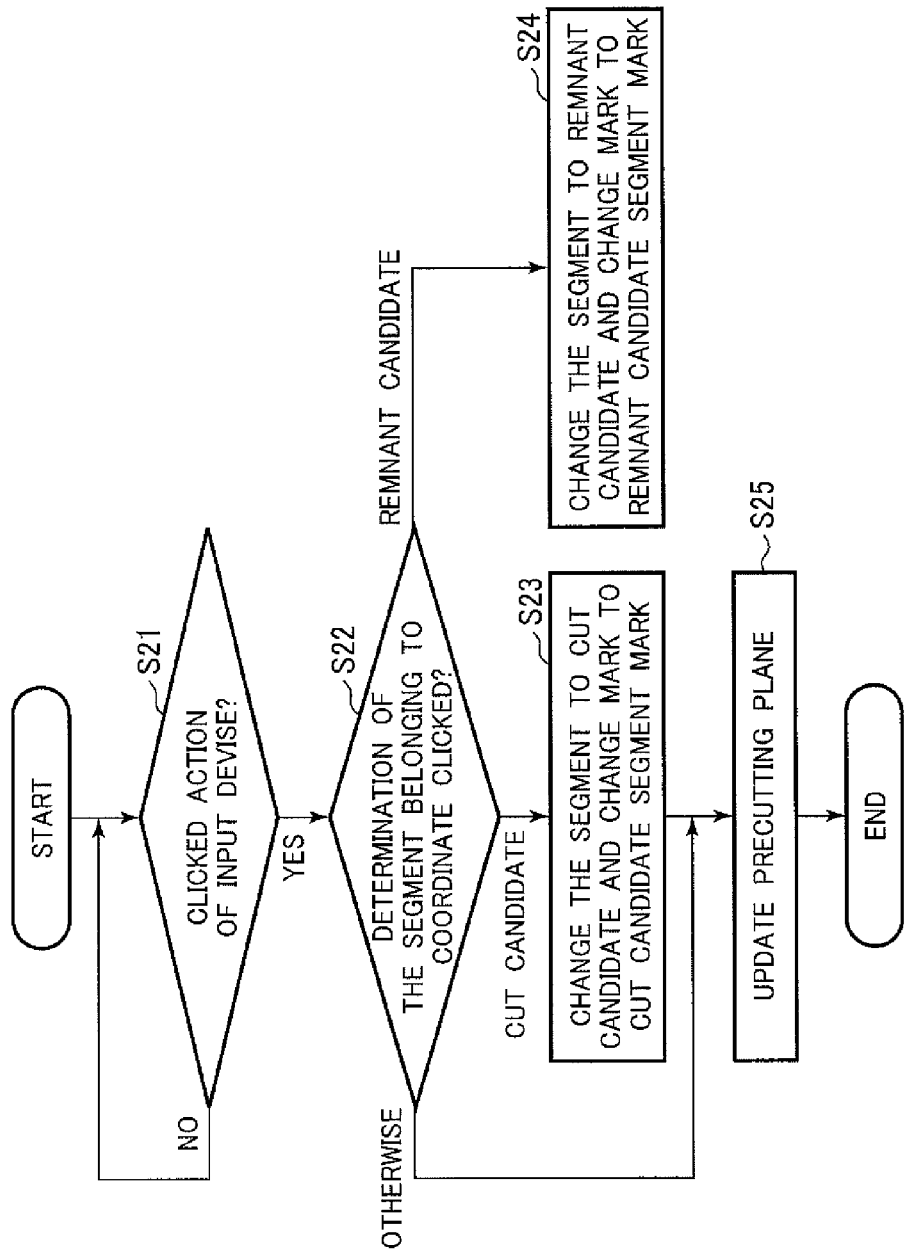
FIG. 7 is a flowchart showing steps of modifying a precutting plane according to a second embodiment of the invention.
Figure 8:
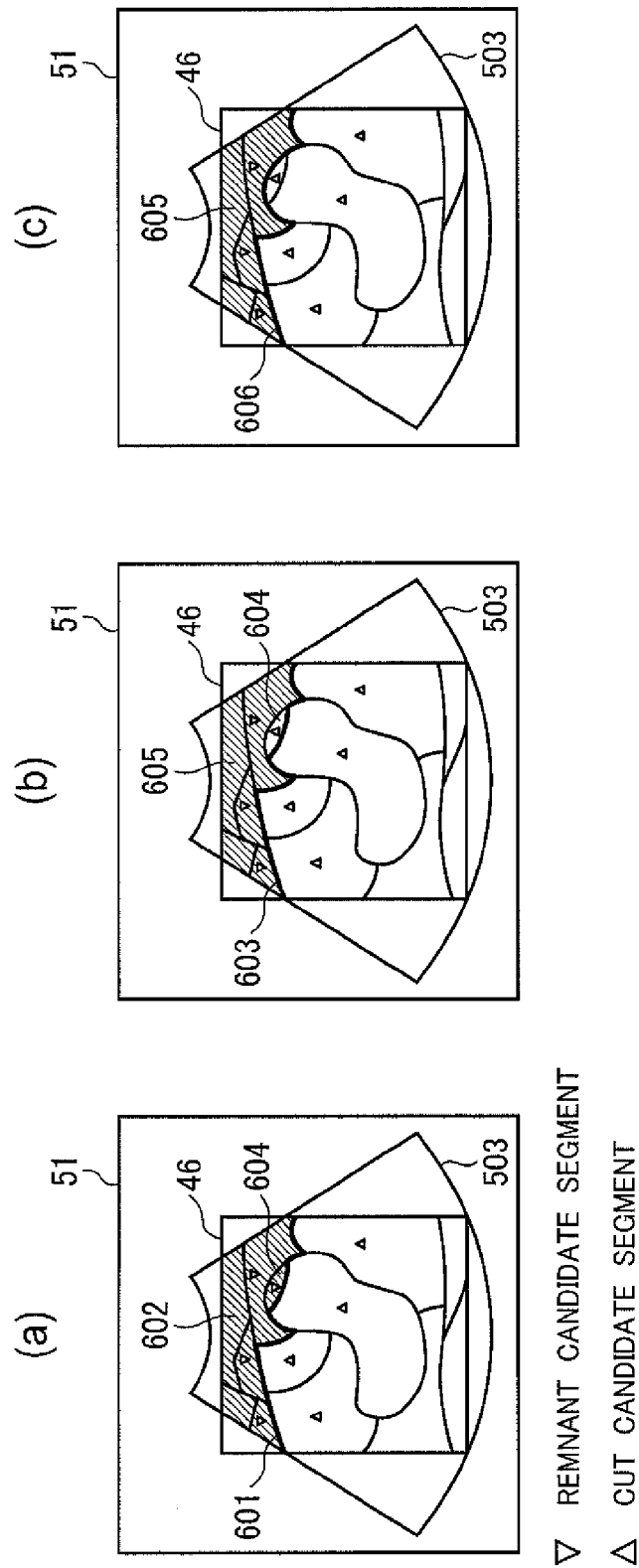
FIG. 8 is diagram showing how a precutting plane can be modified in the procedure shown in FIG. 7.
Figure 9:
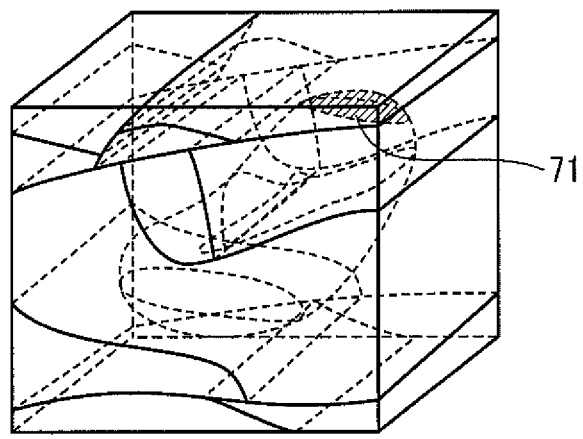
FIG. 9 is a diagram showing modified voxel image data after some voxel data are deleted according to the steps shown in FIG. 7.

Embodiment 2 has an extra feature in that the setting of a precutting plane can be changed. FIG. 7 shows in flowchart a precutting plane alteration procedure. In this embodiment, a precutting plane can be changed in units of segments. Suppose now that a precutting plane setting screen 51 as shown in FIG. 8 is displayed on the display unit 6. FIG. 8(a) shows a cross-section region image 503 superimposed with a precutting plane 601 and ROI46, which is a group of segments 602 to be deleted. As shown in FIG. 9, of the segments shown on the precutting plane setting screen 51, those segments in contact with the precutting plane 601 are marked with either marks of 'remnant candidate segments' (inverted triangle mark ▽) or 'cut candidate segments' (△). Those remnant candidate segments (inverted triangular mark ▽) are segments to be deleted in the embodiment 1, which are not deleted by diagnostician's arbitrary decision in the embodiment 2 but instead left undeleted, that is, they are regarded as remnant candidate segments. On the other hand, contrary to the remnant candidate segments, cut candidate segments (△) are those segments that are not deleted in the embodiment 1 but deleted (or cut) in the embodiment 2. Marks to be used for 'remnant candidate segments' and 'cut candidate segments' are not limited to the marks of the embodiment 2. Instead of marking such segment with the marks, the segments may be bordered with a line of a predetermined style or filled with a predetermined pattern.

As shown in FIG. 8(a), there can exist a segment 604 that is a part of the fetus 44 but located on the side of the precutting plane closer to the viewing point (as indicated by a reference number 71 in FIG. 9). In this case, the diagnostician specifies the segments 604 on the precutting plane setting screen 51 by operating an input device of the input unit 8 such as a track ball and a key board. This will start a precutting plane alteration procedure shown in FIG. 7. First, as the diagnostician clicks on the segment 604, the segment 604 and its coordinates are specified (S21). Next, a determination is made as to whether or not the segment 604 is either a cut candidate segment or a remnant candidate segment, or else.

If the segment 604 is a cut candidate segment, its mark is changed to the remnant candidate segment mark (S23). On the other hand, if otherwise, its remnant candidate segment mark is changed to the cut candidate segment mark (S24). This changes the property of the segment 604 shown on the precutting plane setting screen 51 from the deletion property to the remnant property, as shown in FIG. 8(b), thereby altering the deleting target segment 604 to a residual segment. At the same time, a segment group 602, which is marked as a deleting target, is changed to a deleting target group 605.

Next, in accord with the property of the segment subjected to such alteration, the precutting plane 601 is renewed (S25). This causes the segment 604 to be taken in the amniotic fluid segment, under the renewed precutting plane 606, as shown in FIG. 8(c).

In this way, through a renewal of a precutting plane in accordance with the embodiment 2, a segment property can be modified between the deleting target and remaining target in units of segments obtained in the region division of the volume image data.

Although the depth of a two-dimensional cross-section region image cannot be observed on the precut setting screen 51 in the embodiment 1, a modification of the shape of a two-dimensional precutting plane can be modified in accordance with the embodiment 2.

Figure 11:
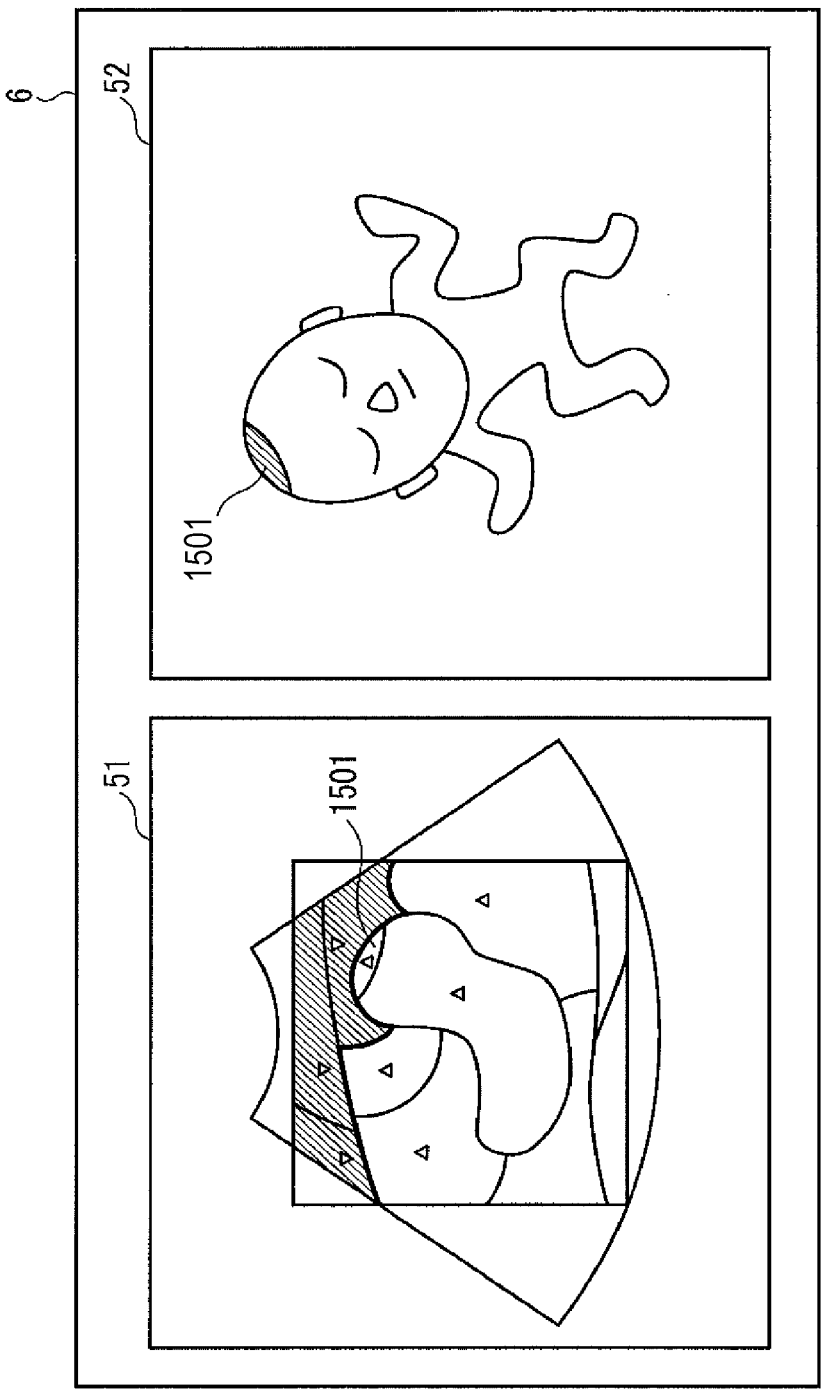
FIG. 11 illustrates a precutting plane resetting screen for resetting a precutting plane in accordance with the procedure shown in FIG. 7, and a three-dimensional image constructed on the basis of the altered precut volume data.

This precutting plane alteration can be achieved in a simple procedure. As shown in FIG. 11, the result of the precut alteration can be confirmed by displaying the precutting plane setting screen 51 and a three-dimensional image 52 of the diagnosing target side by side, and highlighting the segment 1501, whose status has been now changed from the deleting target to the remaining target, and the three-dimensional image that corresponds to the segment 1501. Furthermore, this precutting plane alteration can be done in real time mode while checking the validity of the alteration made by the diagnostician for the observation of the fetus.

In short, since the precutting plane setting screen displays the three-dimensional deleting and remaining regions in different display modes, the diagnostician can easily modify the position of the precutting plane in units of three-dimensional regions upon confirmation of the precutting plane.

Embodiment 3

A precutting plane setting procedure of a third embodiment will now be described with referring to flow-chart shown in FIG. 12. The third embodiment is preferred for a case when a diagnosing target is a fetus. The embodiment 3 utilizes the fact that the fetus is embedded in a large amount of amniotic fluid and that the voxel image data value of the amniotic fluid is smaller than voxel image data value of the fetus so that the amniotic fluid and the fetus can be easily distinguished.

Figure 12:
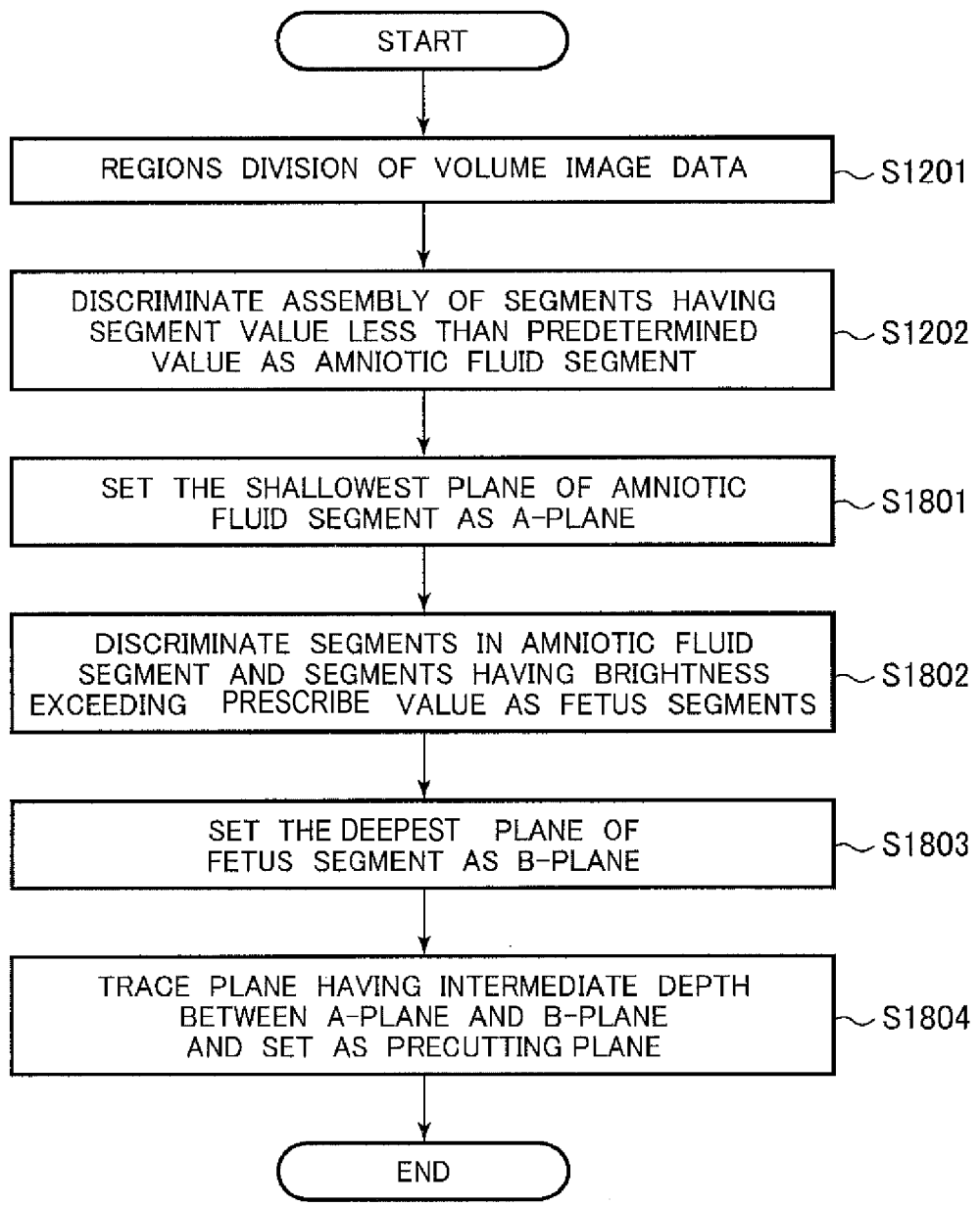
FIG. 12 is a flowchart showing a procedure of modifying a precutting plane according to a third embodiment of the invention.
Figure 13:
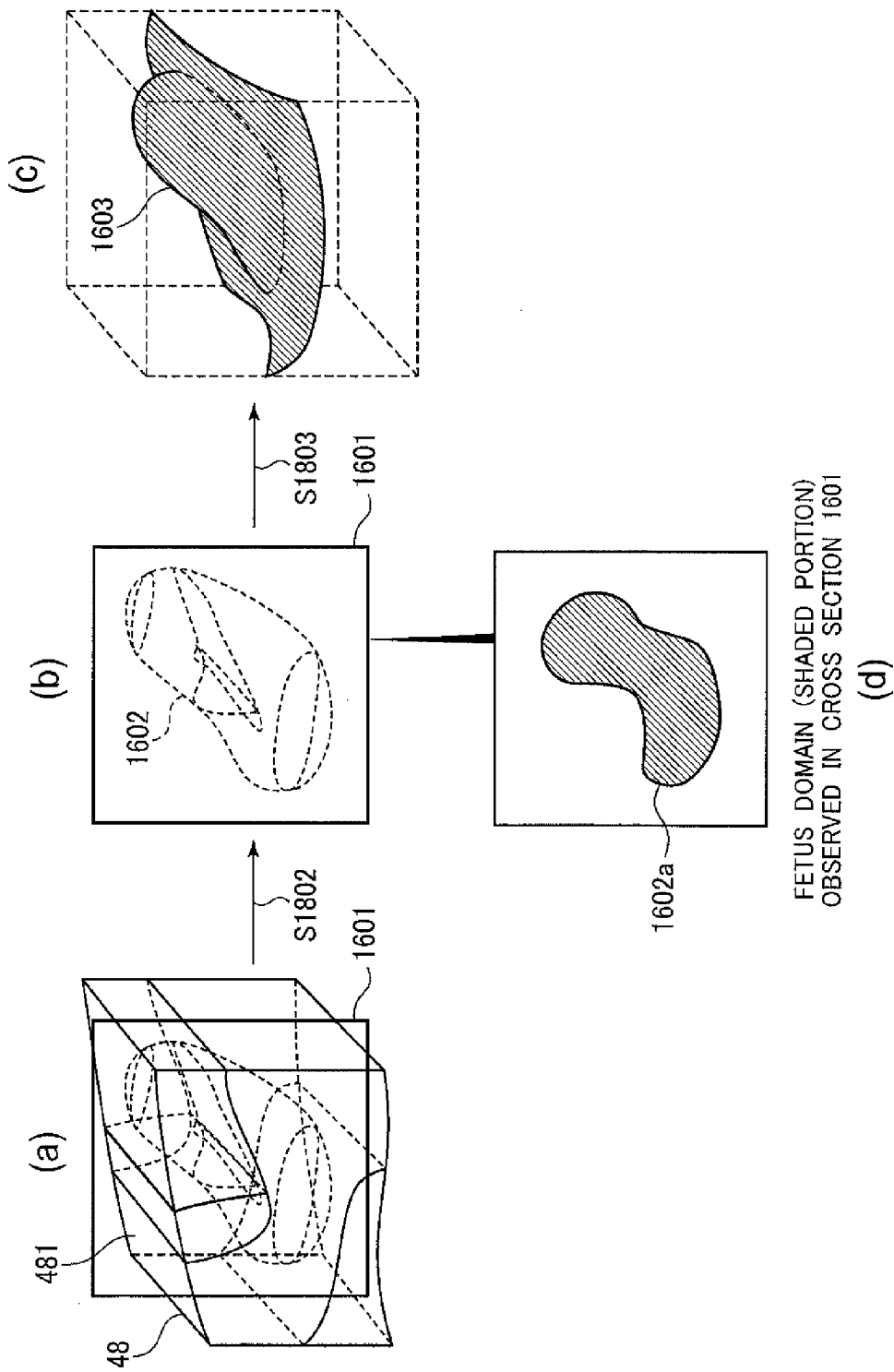
FIG. 13 shows a procedure of setting up a precutting plane according to the third embodiment shown in FIG. 12.

As shown in FIG. 12, the volume image data are first divided into corresponding three-dimensional regions based on the voxel image data of brightness (Step 1201). This image data dividing procedure is the same as the Step S12 of FIG. 4. In the embodiment 3, however, it is preferred to divide the region of the amniotic fluid by solely discriminate the amniotic fluid region, since regions other than the region of the fetus are deleted. To do this, in the embodiment 3, a segment group of segments having less density than a predetermined density for discriminating the amniotic fluid density are divided as the segment of the amniotic fluid region (S1202). This situation is shown in FIG. 13(a). As shown in FIG. 13(a), the coordinates of the shallowest plane 491 (hereinafter referred to as A-plane) of the amniotic fluid segment 48 are stored in a magnetic disc device 52 or in the RAM 53 Step S1801). Next, the segment group is found in the amniotic fluid segments 48 and a typical density of the segment exceed the amniotic fluid discriminating value are recognized as fetus segment 1602, as shown in FIG. 13(b) (Step S1802). Next, the coordinates of the shallowest plane 1603 (hereinafter referred to as B-plane) of the fetus segments are stored in the magnetic disc 52 or RAM 53 (Step S1803).

Figure 14:
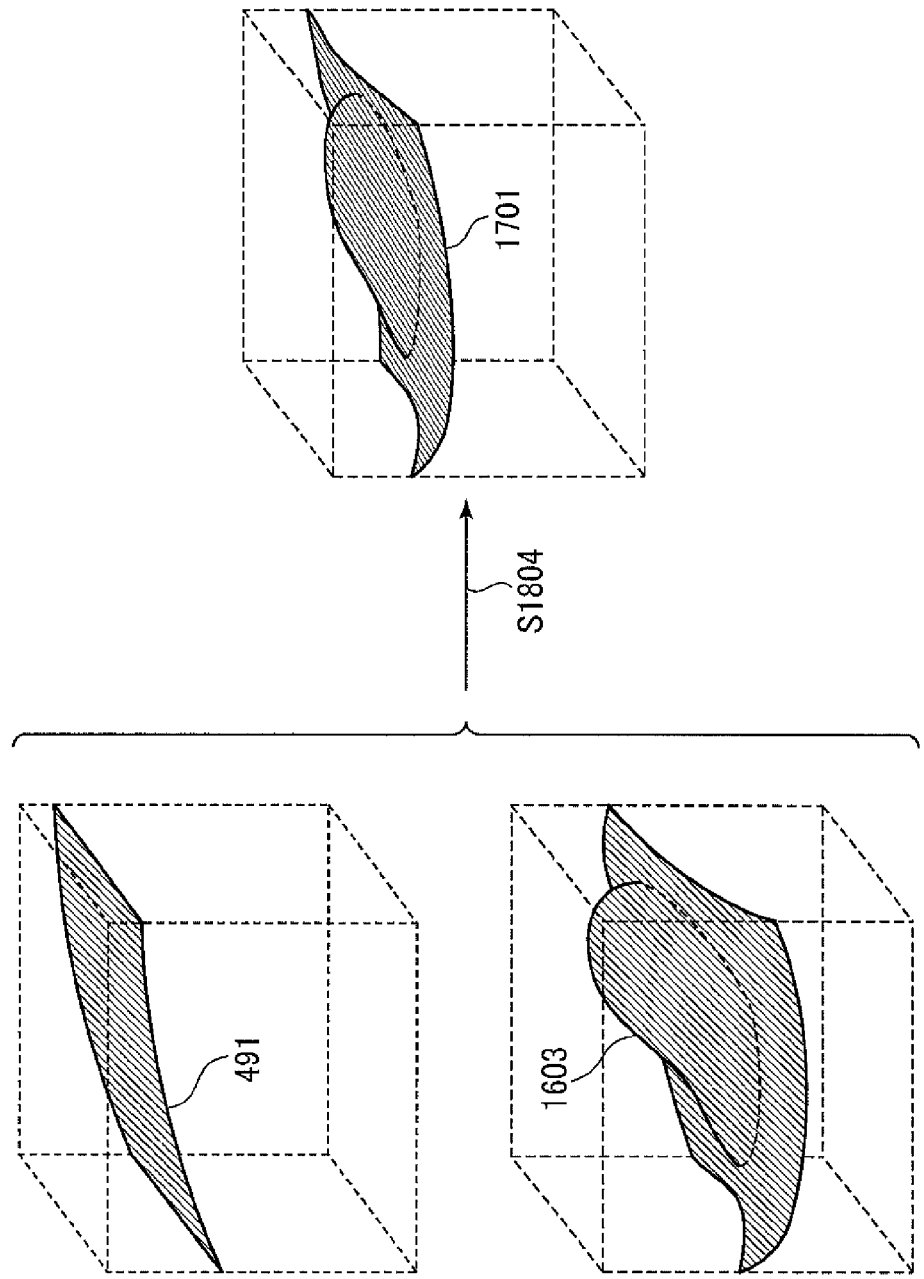
FIG. 14 shows a procedure of setting up a precutting plane according to the third embodiment shown in FIG. 12.

Next, voxels having an intermediate depth between those of A-plane 491 and B-plane 1603 are traced as shown in FIG. 14, and the resultant plane 1701 is defined to be the final precutting plane (Step S1804).

According to the embodiment 3, a precutting plane can be set up in a three-dimensional region which is away from both the placenta and the fetus, adding to the technical advantages of the embodiments 1 and 2, because voxels of voxel image data having voxel values less than a predetermined set value associated with the diagnosing target of fetus are discriminated as neighboring voxels adjacent the three-dimensional fetus region, that is voxels of the amniotic fluid segments, and set up the precutting plane closer to the viewing point than the fetus in the neighboring voxels of the three-dimensional region. Consequently, a risk can be avoided in which deletion of voxel image data of the placenta is incomplete or fetus's voxel image data is excessively deleted.

(Exemplary Display Mode)

Figure 15:
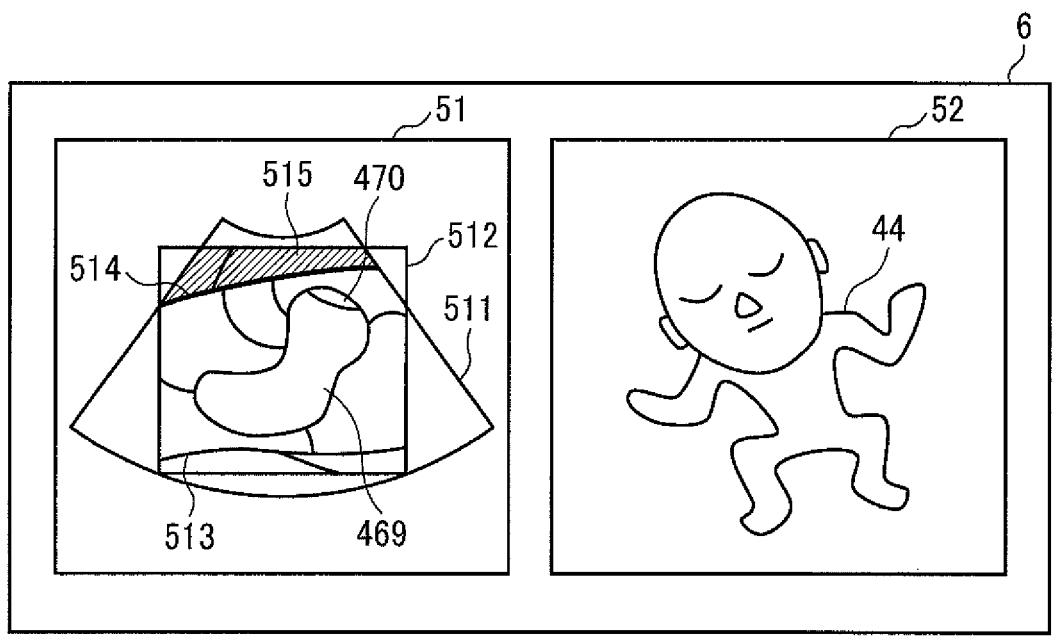
FIG. 15 illustrates a precutting plane setting screen along with an exemplary three-dimensional image of a diagnosing object constructed.

As an example, different display modes of images displayed on the display unit 6 in accordance with the inventive medical imaging apparatus will be described. Display modes used in the present embodiment are as follow. FIG. 15 shows an image for use in the precutting plane setting procedure, displayed on the display unit 6 in one display mode in accordance with the embodiment 1. In FIG. 15, a precutting plane setting screen 51 and a three-dimensional image 52 of a diagnosing target are displayed side by side. In short, the precutting plane setting screen 51 shows an ultrasonic image 511, ROI 512, a boundary 513 of segments constructed in region division, a precutting plane 514, and a property 515 indicative of deleting segments, all superposed together. The ROI 512, segment boundary 513, and precutting plane 514 are three-dimensional figures by nature, but they are shown in cross sections taken along the same plane as the cross-section region image 511.

In order to discriminate groups of segments associated with volume image data to be deleted from groups of segments associated with remaining volume image data, they are marked with different styles of colors, opacities, patterns, and border line properties including thickness, color, and style of border lines in such a way that one or more of the styles can be interchangeably altered. In FIG. 15 for example, the segment border 513 is indicated by a solid line. In addition, groups of segments 515 to be deleted are shadowed with oblique lines.

Figure 16:
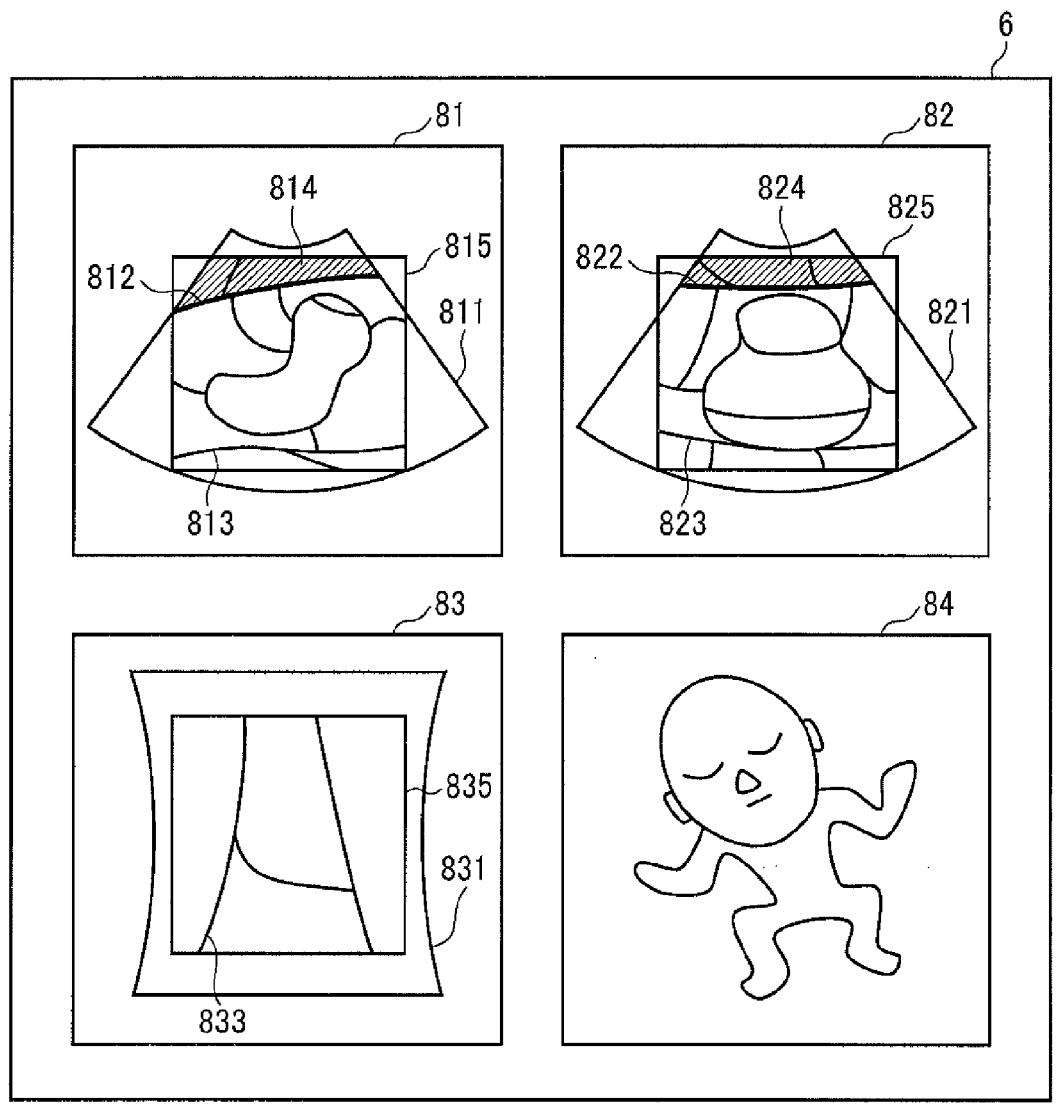
FIG. 16 illustrates a precutting plane setting screen along with an exemplary three-dimensional image of a diagnosing target constructed from precut volume image data.

FIG. 16 shows another example of display mode. FIG. 16 illustrates precutting plane setting screens 81, 82, and 83 associated with plural number of different cross-section region planes side by side with a three-dimensional image 84 of a diagnosing target formed on the basis of precut volume image data generated on the precutting planes set up via the precutting plane setting screens. The first precutting plane setting screen 81 and the second precutting plane setting screen 82 are associated with different cross-section region images 811 and 821, respectively. The third precutting plane setting screen 83 is associated with a still different cross-section region image 831.

Figure 10:
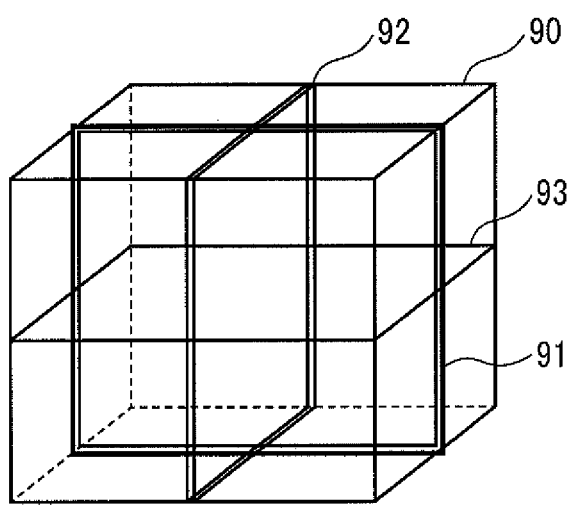
FIG. 10 explains the three orthogonal cross sections shown in FIG. 8.

To note, the cross-section region images 811, 821, and 831 are images that appear in the three orthogonal cross sections 91, 92 and 93 of the same volume image data 90 shown in FIG. 10. Positions of these cross-section regions can be changed using for example a track ball or a keyboard of the input unit 8. Then the cross-section region images are changed in accord with its movement. Precutting planes 812 and 822 are the same three-dimensional precutting plane, which is updated in association with the movements of the three orthogonal cross sections 91, 92, and 92. Display modes of segment boundaries 813, 823, and 833 are also moved in association with the movement of the three orthogonal cross sections 91, 92, and 93, and updated as post-move segment boundaries. Similarly, segment groups 814 and 824 to be deleted are also moved in association with the three orthogonal cross sections 91, 92, and 93, and updated to show the boundaries of the segment groups that appear on the moved three cross sections. Similarly, ROI 815, 825, and 835 are also moved to the positions of the three orthogonal cross sections 91, 92, and 93, and updated to show the boundaries of the ROI on the corresponding cross sections.

The alteration of a precutting plane described above with reference to FIG. 7 involves operation of a graphic user interface (GUT), with reference to a cross-section region image taken along a cross sections of volume image data displayed on the display unit 6 and three-dimensional image of the volume image data. By performing such GUI operation on the precutting plane setting screens 81 and 82 as shown in FIG. 16, the diagnostician can alter the displayed precutting plane while moving the cross sections 91, 92, and 93 of three-dimensional ultrasonic image data via the input unit 8. In this manner, modification of a precutting plane taken along a certain cross section can be achieved while confirming the validity of the precutting plane, thereby permitting the diagnostician to set up an optimum precutting plane for imaging of a fetus.

Figure 17:
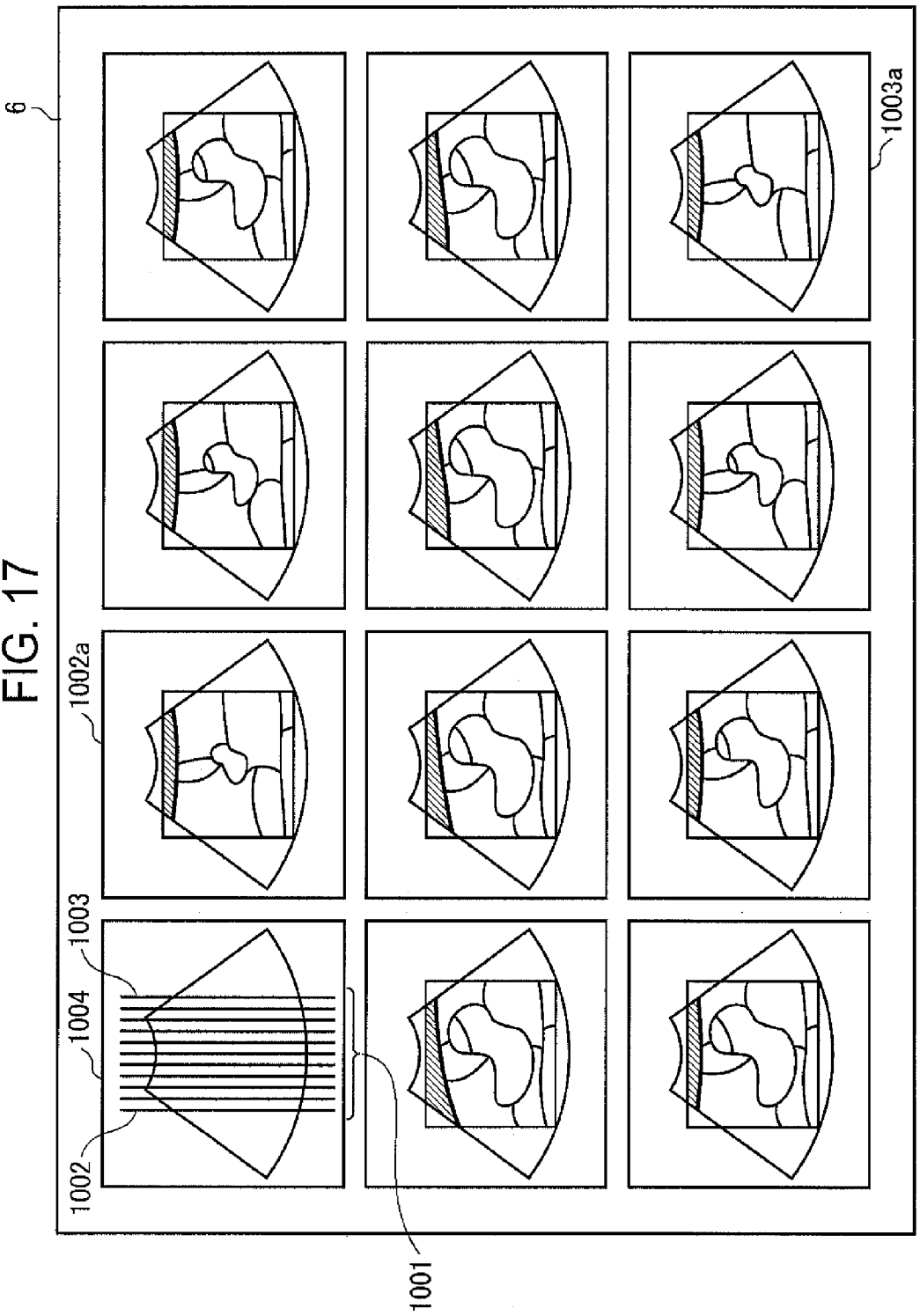
FIG. 17 illustrates another precutting plane setting screen.

FIG. 17 shows another exemplary display mode. FIG. 17 illustrates a series of precut setting screens shown for cross-section region images taken along multiple cross sections. In FIG. 17, the upper left picture (referred to as cross sectional position indication picture) 1004 shows positions of multiple parallel cross sections spaced apart in the direction perpendicular to cross-section region images. For example, plural numbers of lines 1001 show positions of multiple cross sections. The image 1002a shows a cross-section region image and a corresponding precutting plane setting screen taken along the left most cross section 1002. Similar sets of a cross-section region image and a precutting plane setting screen taken along the respective cross sections are shown in sequence in FIG. 17. The lower right image 1003a shows a set of such cross-section region image and a precutting plane setting screen taken along the cross section1003. Such collective presentation of cross-section region images and precutting planes enables ultrasonic diagnosis in continuous tomography and stereoscopic resetting of precutting planes, which improves efficiency of a diagnosis. The number of displayable cross sections can be changed by the input unit 8.

FIG. 18 illustrates a precutting plane setting screen in accordance with another type of display mode. FIG. 18 shows a precutting plane setting screen 51 configured to display a precutting plane 1103, which is superimposed with deleting segment group 1104 shaded to a certain degree of opacity. The precutting plane setting screen 51 can display superposition of segments associated with multiple cross sections by shading them at different opacities. In this display mode, those segments that are normally invisible from underneath other segments (e.g. portion 1101 for example) are made visible, thereby facilitating resetting of a precutting plane easier. An additional light-and-shade bar 1102 indicating different depths may be displayed. The bar 1102 may be a gray scale or may be a color gradation scale.

The inventions of medical imaging apparatus and medical image constructing method have been described above with reference to a few embodiments. Particularly, use of the apparatus and the method has been shown and described in connection with observation and diagnosis of a fetus utilizing three-dimensional images thereof constructed by the invention. However, the invention is not limited to this use. Instead, the invention may be used equally well to obtain volume image data and display three-dimensional images of diagnosing targets in observations such as a liver, liver cells, hepatic blood vessels, a gallbladder, bile ducts, a spleen, pancreas, kidney, adrenal gland, womb, ovary, prostate gland, stomach, intestines, vermiconstruct appendix, heart, blood vessels including arteries and veins, a thyroid gland, parathyroid, carotid, jugular, mammary glands, a lymph node, digestive organs, ureter, and a bladder as well as in the observation of biological tissues and muscular tissues.

BRIEF DESCRIPTION OF SYMBOLS 5 image constructing unit,
6 display unit,
7 control unit,
8 input unit

The invention claimed is:

1. A medical imaging apparatus, comprising:
an image constructing unit, executed by a processor, that acquires volume image data composed plural number of cross-section region image data of a diagnosing object obtained on the plural number of cross sections perpendicular to a line passing through the cross-section region images, and that constructs a three-dimensional images of a diagnosing target inside of the diagnosing object as seen from a set viewing point using the volume image data;
a display that displays the cross-section region images of the diagnosing object or the three dimensional image of the diagnosing target;
an input unit, executed by a processor, that inputs parameters, including parameters that set up a precutting plane at an inter-voxel image data boundary between the voxel image data closer to the set viewing point than the voxel image data associated with the diagnosing target of the diagnosing object and the voxel image data associated with the diagnosing target of the diagnosing object, using the cross-section region images of the diagnosing object displayed on the display; and
a controller that controls the configuration of the three dimensional image constructed by the image constructing unit on the basis of the precutting plane set via the input unit, wherein the controller extracts the inter-voxel image data boundary between the voxel image data based on a threshold value included in the parameters, resets the precutting plane using the extracted boundary, and controls the image constructing unit to re-construct the three dimensional image of the diagnosing target based on the basis of the reset precutting plane, wherein the controller comprises:
a region discrimination unit, executed by a processor, that discriminates the three-dimensional region of the three-dimensional image consisting of voxels associated with the diagnosing target, based on the voxel image data within a predetermined voxel image data, and
a region division unit, executed by a processor, that divides the volume image data into plural number of three-dimensional regions based on the voxel values of the plural number of voxels,
wherein, the region discrimination unit discriminates, based on the voxel values of the respective volume image data divided by the region division unit, the three-dimensional region associated with the diagnosing target and a three-dimensional region adjacent the diagnosing target,
wherein the image constructing unit constructs:
a cross sectional image taken on an arbitrary cross section of plural number of three-dimensional regions and indicates the plural number of three-dimensional regions, and
an overall three-dimensional image of the multiple three-dimensional regions, based on the volume image data divided by the region division unit, and
wherein the image constructing unit comprises a precutting plane setting screen construction unit, executed by a processor, that constructs a precutting plane setting screen where a boundary line or plane of the divided three-dimensional regions and a precutting line or plane set by the input unit were superposed on the cross-sectional image and displays the screen on the display,
wherein the image constructing unit further constructs, and displays on the precutting plane setting screen in different display modes, a three-dimensional region to be deleted and a three dimensional region to be left undeleted,
wherein, upon designating a three-dimensional region in contact with or adjacent to the precutting plane or line displayed on the precutting plane setting screen via the input unit, the precutting plane setting screen constructing unit moves the precutting plane in contact with the three-dimensional region towards, or away from, the viewing point, and
wherein the precutting plane setting screen constructing unit selects a three-dimensional region in contact with the precutting plane on one side of the precutting plane closer to the viewing point as a candidate region to be left undeleted, and selects a three-dimensional region in contact with the precutting plane on the other side of the precutting plane with respect to the viewing point as the candidate region to be deleted, and
displays these candidate regions in distinguishable display modes using different marks, colors, or representations.

2. The medical imaging apparatus according to claim 1, wherein the region discrimination unit discriminates the voxel image data as neighboring voxels surrounding the three-dimensional region associated with the diagnosing target, on the basis of each of the voxel image data has a voxel value within a predetermined range.

3. The medical imaging apparatus according to claim 1, wherein the region division unit divides the voxel image data into said plural number of three-dimensional regions by grouping voxel image data such that voxels of each group have voxel values within a tolerance range pertinent to the group.

4. The medical imaging apparatus according to claim 1, wherein the region discrimination unit discriminates at least one of the three-dimensional regions associated with the diagnosing target and the three-dimensional regions adjacent the diagnosing target, based on at least one of physical quantities including voxel image data, difference or gradient of voxel image data between two neighboring voxels, and a combination thereof.

5. The medical imaging apparatus according to claim 1 further comprising:
   wherein the region dividing unit divides the volume image data into plural number of three-dimensional regions based on each of said plural number of voxel image data;
   wherein the region discrimination unit discriminates at least one of the three-dimensional region associated with the diagnosing target and the three-dimensional regions adjacent the diagnosing target based on the voxel image data of the respective three-dimensional regions of the divided volume image data; and
   wherein the image construction unit sets up a precutting plane at a boundary either between the three-dimensional region associated with the discriminated diagnosing object and the three-dimensional regions adjacent the diagnosing target or in the three-dimensional regions adjacent the diagnosing target.

6. A method of constructing medical images, comprising:
   constructing volume image data by acquiring images from plural number of cross-section region images of a diagnosing object in the direction perpendicular to the planes of the cross-section region images;
   constructing three-dimensional images inside of the diagnosing target inside of the diagnosing object as seen from a set viewing point on the basis of the volume image data;
   displaying the cross-section region images or the three-dimensional image of the diagnosing target inside of the diagnosing object;
   entering parameters including precutting plane setting parameters for setting up, utilizing the cross-section region images of the diagnosing object displayed, a precutting plane at an inter-voxel image data boundary between the voxel image data of the volume voxel image data located on one side of the diagnosing target closer to the viewing point and the voxel image data belonging to the diagnosing target; and
   controlling execution of the second step based on the precutting plane set up, wherein the controlling further extracts the inter-voxel image data boundary on the basis of the inter-voxel-image data threshold value inputted in the entering parameters step, resets a precutting plane based on the inter-voxel image data boundary, and executes the entering parameters step based on the reset precutting plane;
   discriminating the three-dimensional region of the three-dimensional image consisting of voxels associated with the diagnosing target, based on the voxel image data within a predetermined voxel image data;
   dividing the volume image data into plural number of three-dimensional regions based on the voxel values of the plural number of voxels;
   discriminating, based on the voxel values of the respective volume image data divided, the three-dimensional region associated with the diagnosing target and a three-dimensional region adjacent the diagnosing target;
   constructing a cross sectional image taken on an arbitrary cross section of plural number of three-dimensional regions and indicating the plural number of three-dimensional regions and an overall three-dimensional image of the multiple three-dimensional regions, based on the volume image data divided;
   constructing a precutting plane setting screen where a boundary line or plane of the divided three-dimensional regions and a precutting line or plane set were superposed on the cross-sectional image and displaying the screen;
   constructing, and displaying on the precutting plane setting screen in different display modes, a three-dimensional region to be deleted and a three dimensional region to be left undeleted,
   wherein, upon designating a three-dimensional region in contact with or adjacent to the precutting plane or line displayed on the precutting plane setting screen via the input unit, moving the precutting plane in contact with the three-dimensional region towards, or away from, the viewing point; and
   selecting a three-dimensional region in contact with the precutting plane on one side of the precutting plane closer to the viewing point as a candidate region to be left undeleted, and selecting a three-dimensional region in contact with the precutting plane on the other side of the precutting plane with respect to the viewing point as the candidate region to be deleted, and
   displaying these candidate regions in distinguishable display modes using different marks, colors, or representations.

* * * * *